(12) United States Patent
Schoeder et al.

(10) Patent No.: US 10,962,534 B2
(45) Date of Patent: Mar. 30, 2021

(54) METHOD FOR THE IMMOBILIZATION OF BIOMOLECULES

(71) Applicant: Boehringer Ingelheim Vetmedica GmbH, Ingelheim am Rhein (DE)

(72) Inventors: Heinz Schoeder, Isernhagen (DE); Matthias Griessner, Hannover (DE); Frank Leenders, Berlin (DE); Ralf Kraehmer, Panketal (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 662 days.

(21) Appl. No.: 15/435,438

(22) Filed: Feb. 17, 2017

(65) Prior Publication Data
US 2017/0241998 A1 Aug. 24, 2017

(30) Foreign Application Priority Data
Feb. 22, 2016 (EP) .................... 16156777

(51) Int. Cl.
| | | |
|---|---|---|
| *G01N 33/543* | (2006.01) | |
| *C07K 1/107* | (2006.01) | |
| *C07K 17/14* | (2006.01) | |
| *G01N 33/553* | (2006.01) | |

(52) U.S. Cl.
CPC ..... *G01N 33/54353* (2013.01); *C07K 1/1077* (2013.01); *C07K 17/14* (2013.01); *G01N 33/54393* (2013.01); *G01N 33/553* (2013.01)

(58) Field of Classification Search
None
See application file for complete search history.

(56) References Cited

U.S. PATENT DOCUMENTS

| | | | |
|---|---|---|---|
| 6,225,443 | B1 | 5/2001 | DeMars et al. |
| 7,531,181 | B2 | 5/2009 | Danishefsky et al. |
| 2010/0041077 | A1 | 2/2010 | Nagy et al. |

FOREIGN PATENT DOCUMENTS

| | | |
|---|---|---|
| EP | 1826564 A1 | 8/2007 |
| JP | 2011-503517 A | 1/2011 |
| JP | 2012-233878 A | 11/2012 |
| WO | 0015255 A1 | 3/2000 |
| WO | 2008099284 A2 | 8/2008 |
| WO | 2009080719 A1 | 7/2009 |
| WO | 2009089568 A1 | 7/2009 |
| WO | 2011041586 A1 | 4/2011 |
| WO | 2012079030 A2 | 6/2012 |

OTHER PUBLICATIONS

Mei, Bing C., et al. "Modular poly (ethylene glycol) ligands for biocompatible semiconductor and gold nanocrystals with extended pH and ionic stability." Journal of Materials Chemistry 18.41 (2008): 4949-4958. (Year: 2008).*

Su, Xiaoye, et al. "Mild two-step method to construct DNA-conjugated silicon nanoparticles: Scaffolds for the detection of microRNA-21." Bioconjugate chemistry 25.10 (2014): 1739-1743. (Year: 2014).*

Ortiz, Ricardo Acosta, et al. "Preparation of a crosslinked sucrose polymer by thiol-ene photopolymerization using dithiothreitol as connnononner." Carbohydrate Polymers 82.3 (2010): 822-828. (Year: 2010).*

"ACA-PEG-SH, Acrylamide-PEG-Thiol". Biochempeg Products Catalog Accessed at [http://www.biochempeg.com/product/Product.asp?Pro_ID=207] retrieved on Mar. 15, 2017, 1 page.

"Propargyl-PEG4-thiol". BroadPharm Products Catalog, accessed at [https://www.braodpharm.com/web/product.php?catalog=BP-23139] retrieved on Mar. 15, 2017, 1 page.

International Search Report and Written Opinion for PCT/EP2017/053601 dated Apr. 19, 2017.

Kendziora et al., "Multifunctional linker for orthogonal decoration of gold nanoparticles with DNA and protein." RSC Advances, vol. 4, No. 35, Apr. 3, 2014, pp. 17980-17985.

Zianhua et al., "Self-Assembled Monolayer of Lipoic Acid on Gold and Its Application to Rapid Determination of 2, 3, 7, 8-Tetrachlorodibenzo-p-Dioxin". Transactions of Tianjin University, vol. 19, No. 4, Aug. 2013, pp. 248-254.

* cited by examiner

*Primary Examiner* — Robert J Yamasaki

(74) *Attorney, Agent, or Firm* — Edell, Shapiro & Finnan, LLC

(57) ABSTRACT

The invention relates to a method for the immobilization of biomolecules containing at least one sulfhydryl group, which method comprises contacting a modified metal surface with the biomolecule irradiating the resulting surface with UV radiation in the presence of a photo-initiator, wherein said metal surface is modified with a cross-linker compound comprising a terminal thiol or dithiol group covalently linked to the metal surface, a spacer group, which at the other terminal end is carrying an isolated double or triple bond.

5 Claims, 3 Drawing Sheets

METHOD FOR THE IMMOBILIZATION OF BIOMOLECULES

A. FIELD OF THE INVENTION

Figure 1:
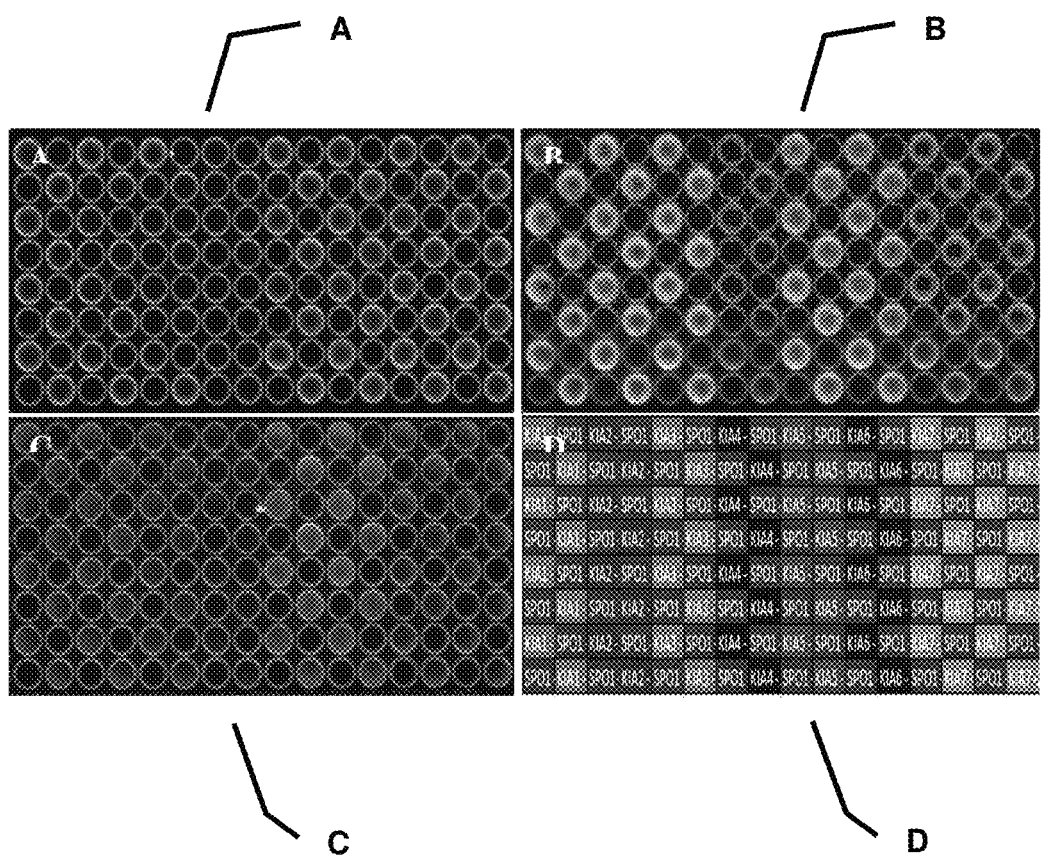

The invention relates to a method for the immobilization of biomolecules containing at least one sulfhydryl group, which method comprises contacting a modified metal surface with the biomolecule irradiating the resulting surface with UV radiation in the presence of a photo-initiator, wherein said metal surface is modified with a cross-linker compound comprising a terminal thiol or dithiol group covalently linked to the metal surface, a spacer group, which at the other terminal end is carrying an isolated double or triple bond.

B. DESCRIPTION OF THE RELATED ART

Detection and quantification of analytes, such as biomolecules or other molecules that affect biological processes, present in samples are integral to analytical testing. For example, the detection of biomolecules that are markers of biological activity or disease is important for the diagnosis of medical conditions and pathologies. However, converting the detection of an analyte, such as a biomolecule, into a usable signal is challenging in part due to the complexity of transducing the detection event, for example antibodies binding an antigen, into a detectable signal that can be converted into perceivable data. Some assays, such as enzyme linked immunoabsorbant assays (ELISA) detect biomolecules by monitoring the binding event which generates light or a reaction product that produces a color change in the sample. One advantage of these types of assays is that they are very sensitive. However, a drawback of these assays, such as an ELISA assay, is that they typically require long period of time to develop a detectable signal and require multiple steps to complete.

Recently, other methods have been being developed that retain the sensitivity of traditional immunoassays, while eliminating the complexity and time involved in developing the signal. One strategy is to couple the sensitivity of the immunoassay, for example by using highly selective antibodies that have high affinity for analytes, with electrochemical measurements. By combining the detection events to an electric signal, the information about the presence and concentration of an analyte in a sample can be immediately converted to an electrical signal. Over the past decades several sensing concepts and related devices have been developed. The most common traditional techniques include cyclic voltammetry, chronoamperometry, chronopotentiometry, and impedance spectroscopy.

However, the general performance of electrochemical sensors is often determined by the surface architectures that connect the sensing element to the biological sample at the nanometer scale. Electrochemical biosensors have suffered from a lack of surface architectures allowing high enough sensitivity and unique identification of the response with the desired biochemical event.

Thus, the need exists for electrochemical bio sensors that have the high sensitivity of traditional assays, such as ELISA assays, while maintaining the desirable aspects of an electrochemical sensor, such as readily measurable signal and the prospects of miniaturization.

The US patent application US 2012/0228155 relates to a method of making a functionalized electrode for detecting a target analyte, comprising: contacting an electrically conducting surface, e.g. a gold electrode with a mixture comprising a first thiol compound having a terminal amino group and a second thiol compound having a terminal OH, an alkoxy, a methyl, a sugar, a zwitter-ionic, or a polar non-ionic group, wherein sulfhydryl groups on the first and second thiol compounds bond with the electrically conducting surface, thereby creating a monolayer on the surface of the electrically conducting surface; contacting the monolayer on the surface of the electrically conducting surface with a hetero-bifunctional linker that comprises an amine reactive functionality, and a diazirine or maleimide moiety; and contacting the monolayer on the surface of the electrically conducting surface with a ligand that specifically binds a target analyte, thereby making a functionalized electrode for detecting a target analyte.

If the hetero-bifunctional linker comprises sulfo-NHS diazirine (sulfo-SDA), the methods further comprises exposing the monolayer on the surface of the electrically conducting surface to UV radiation, thereby making a functionalized electrode for detecting a target analyte. The U.S. Pat. No. 8,580,571 relates to a method for producing a biosensor comprising a substrate to which a hydrophilic polymer is being bound, the method comprising the following steps: forming a self-assembled monolayer on a substrate, wherein the self-assembled monolayer is formed by an alkanethiol; coating a solution containing a photo radical generator onto this substrate to allow the photo radical generator to bind to the self-assembled mono-layer on the substrate, coating a solution containing a hydrophilic polymer onto this substrate, wherein the hydrophilic polymer is a polysaccharide having a carboxyl group and a double bond and exposing this substrate to light to generate a reactive group from the photo radical generator and to covalently bind the hydrophilic polymer to said reactive group via the double bond of the hydrophilic polymer, whereby the biosensor comprising a substrate to which a hydrophilic polymer is being bound is produced, wherein the carboxyl group contained in the hydrophilic polymer bound to the substrate in the biosensor is used for immobilizing a physiologically active substance of interest onto the biosensor.

The Chinese patent application CN 104 597 230 suggests a method for manufacturing a functionalized polymer film, comprising the following steps: forming a terminally functionalized self-assembly mono-molecular layer on a surface of the substrate of a biochip, e.g. a terminally functionalized thiol or dithiol compound linked to a gold surface; grafting a photo-cross-linker to the terminal of the self-assembly mono-molecular layer by chemical bonding, e.g. a phenyl-diazirine; spin-coating a polymer solution on the resulting surface formed; and performing an UV irradiation on the biochip having the spin-coated polymer surface to form a chemical bonding under the UV light to have the polymer grafted to the surface to form a polymer film.

SHORT SUMMARY OF THE INVENTION

Accordingly the invention relates to a method for the immobilization of biomolecules containing at least one sulfhydryl group, which method comprises the steps of:
a) optionally treating a biomolecule with an reducing agent in order to cleave existing —S—S— bridges in the biomolecule, or
b) optionally treating a biomolecule with an acylation agent carrying a protected sulfhydryl group and deprotecting the sulfhydryl group;
c) contacting a modified metal surface with the biomolecule;

d) irradiating the resulting surface with UV radiation in the presence of a photo-initiator, wherein said metal surface is modified with a cross-linker compound comprising:
  i) a terminal thiol or dithiol group covalently linked to the metal surface being connected to
  ii) a spacer group, which at the other terminal end is carrying an isolated C—C-double or C—C-triple bond.

Furthermore, the invention relates to a compound of formula (I),

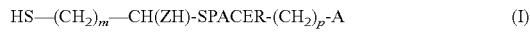

in which
m is an integer from 2 to 6,
A is selected from —CH=CH$_2$ and —C≡CH, and
Z is S or a single bond,
SPACER is a group of formula

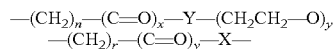

wherein
X and Y are each independently NH or O,
n is 0 or an integer from 1 to 10,
x and v are each independently 0 or 1,
y is an integer from 1 to 20,
r and p are each independently selected from an integer from 1 to 6.

Another aspect of the invention is an intermediate of formula (II),

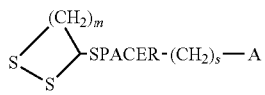

wherein A, SPACER, m and s have the meaning given for formula (I).

Furthermore, the invention relates to a modified metal surface in which at least one thiol group of the compound of formula (I) according to the invention is covalently linked to at least one of the metal atoms of the surface.

A final aspect of the invention is a kit for carrying out the method of immobilizing biomolecules, in accordance with the invention, said kit comprising
  i) a substrate with a modified metal surface according to the invention,
  ii) an optional containment unit containing a suitable reducing agent, or
  iii) an optional containment unit containing a suitable acylation agent carrying a protected sulfhydryl group and a deprotection agent for the sulfhydryl group
  iv) a containment unit containing a suitable photo-initiator, and
  v) a leaflet explaining the conditions for carrying out the method.

SHORT DESCRIPTION OF THE DRAWINGS

FIG. 1 shows fluorescence pictures of complementary metal-oxide-semiconductor (CMOS) chips according to the invention under different conditions in comparison with a surface modified with lipoamide-PEG(11)-maleimide. A shows a lipoamide-PEG(11)-maleimide modified surface with 10 min UV irradiation at 304 nm wavelength. B shows an R-α-lipoic-acid-PEG12-propargyl modified surface according to the invention with 7.5 min irradiation time. C shows an R-α-lipoic-acid-PEG12-propargyl modified surface without UV irradiation. It is apparent that only little immobilization of the antibody at the surface takes place without UV irradiation. D shows Spotting-Layout KIA represents different reaction conditions of the polyclonal rabbit anti-ACTH antibody. SPO represents the spotting control, where only the spotting buffer has been applied.

Figure 2:
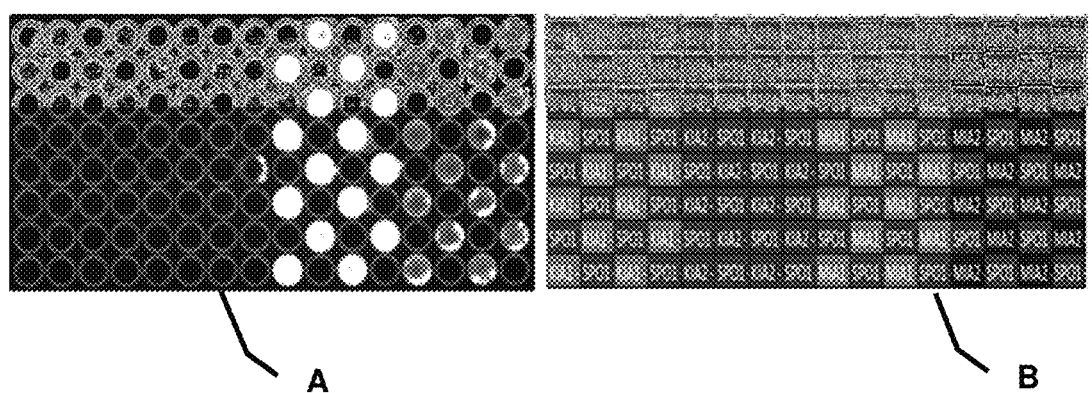

FIG. 2 shows comparison of fluorescence pictures of CMOS chips according to the invention on which a monoclonal mouse antibody has been immobilized with and without use of a photo initiator.

Figure 3:
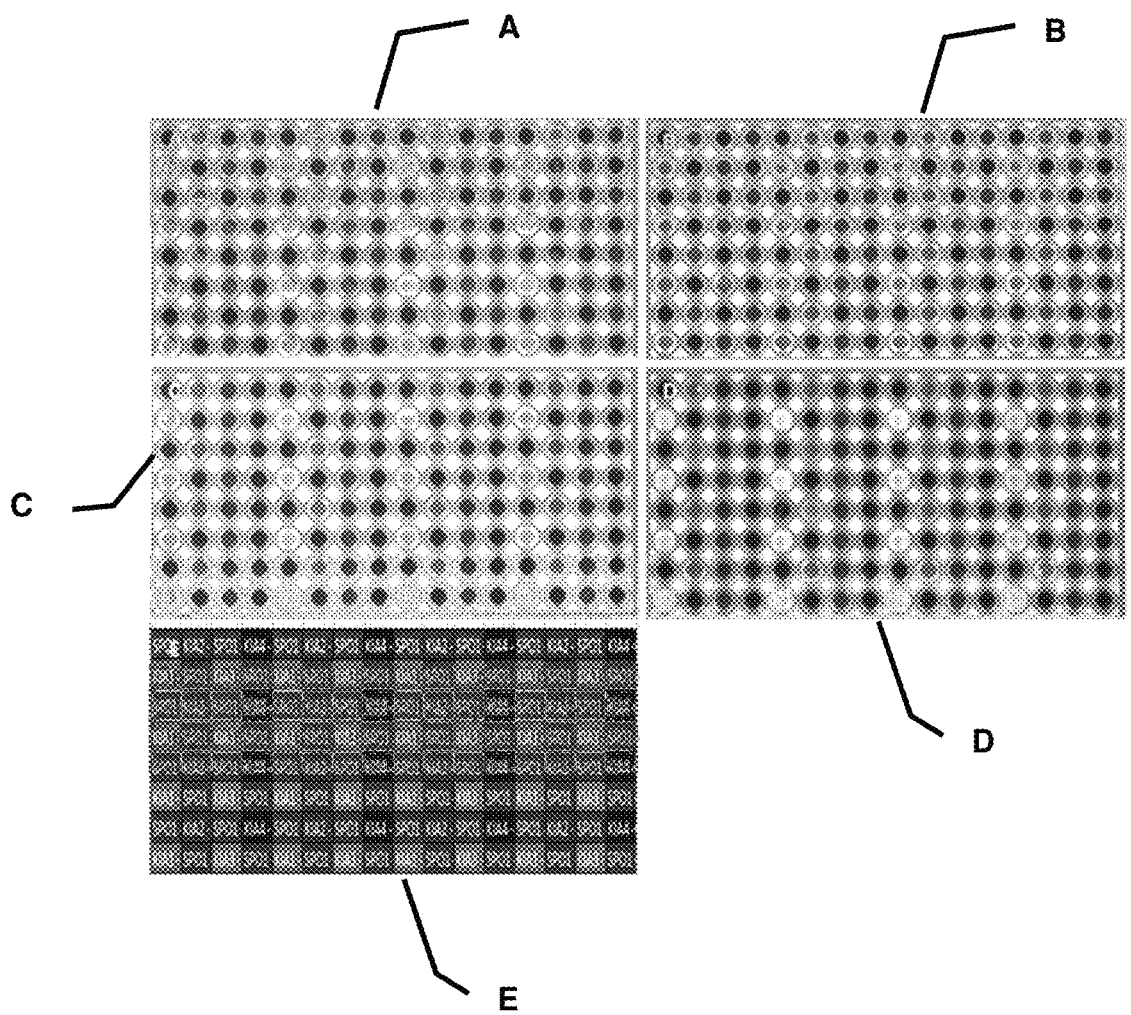

FIG. 3 shows fluorescence pictures of CMOS chips according to the invention on which polyclonal rabbit anti-ACTH-antibodies have been immobilized. A shows the immobilization of a polyclonal rabbit anti-ACTH antibody with the photoreaction according to the invention on different modified surfaces of R-α-lipoic-acid-5 kDa PEG-propargyl (Example 1.5) modified surface. B shows the immobilization of a polyclonal rabbit anti-ACTH antibody with the photoreaction according to the invention on different modified surfaces of R-α-lipoic-acid-PEG12-propargyl (Example 1.2) modified surface. C shows the immobilization of a polyclonal rabbit anti-ACTH antibody with the photoreaction according to the invention on different modified surfaces of R-α-lipoic-acid-5 kDa PEG-allyl (Example 1.4) modified surface. D shows the immobilization of a polyclonal rabbit anti-ACTH antibody with the photoreaction according to the invention on different modified surfaces of R-α-lipoic-acid-PEG12-allyl (Example 1.1) modified surface. E shows the spotting-layout KIA corresponds with a polyclonal rabbit anti-ACTH antibody, wherein KIA shows the highest concentration (100 µg/mL as spotting solution), whereas KIA4 contains the lowest concentration (12.5 µg/mL as spotting solution).

Figure 4:
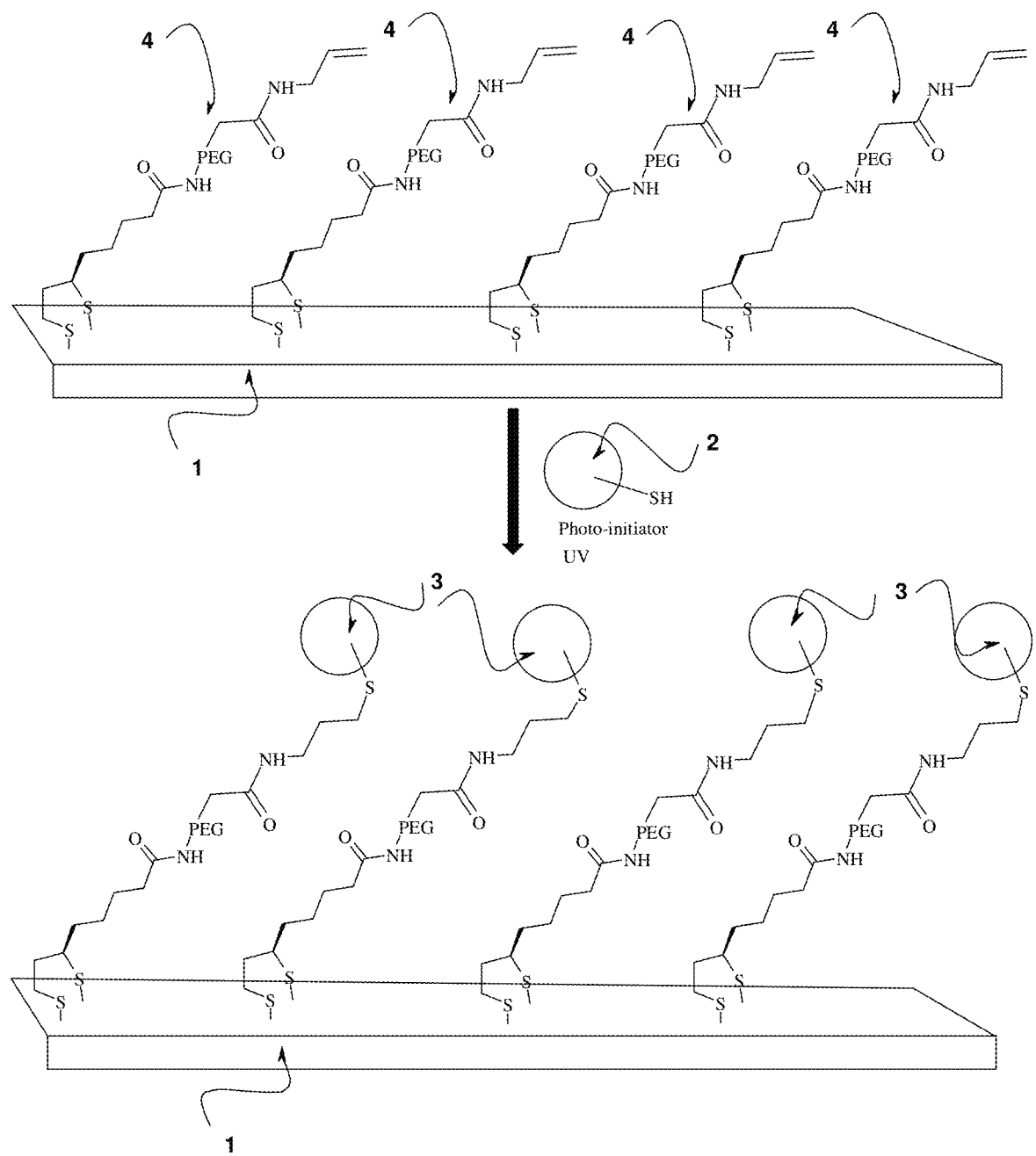

FIG. 4 shows a schematic representation of the immobilization of a biomolecule according to the invention.

DETAILED DESCRIPTION OF THE INVENTION

I. Listing of Terms

Unless otherwise noted, technical terms are used according to conventional usage. Definitions of common terms in molecular biology may be found in Benjamin Lewin, Genes VII, published by Oxford University Press, 2000 (ISBN 019879276X); Kendrew et al. (eds.), The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes". Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. In case of conflict, the present specification, including explanations of terms, will control.

In addition, the materials, methods, and examples are illustrative only and not intended to be limiting.

To facilitate review of the various examples of this disclosure, the following explanations of specific terms are provided:

Biomolecule: A biologically active molecule, which may stem from biological sources or may be produced synthetically.

Allergen: A nonparasitic antigen capable of stimulating a type-I hypersensitivity reaction. Type I allergy is the production of immunoglobulin E (IgE) antibodies against otherwise harmless antigens, termed allergens, which can originate from a multitude of allergen sources (e.g., mites, plant pollens, animals, insects, molds, and food). IgE-mediated presentation of allergens to T cells leads to T-cell activation and chronic allergic inflammation (e.g., chronic asthma, atopic dermatitis), particularly after repeated contact with allergens. This event also induces increases of allergen specific serum IgE levels and patients. Common allergens include: those derived from plants, such as trees, for example *Betula verrucosa* allergens Bet v I, Bet v 2, and Bet v 4; *Juniperous oxycedrus* allergen Jun o 2; *Castanea sativa* allergen Cas s 2; and *Hevea brasiliensis* allergens Hey b I, Hey b 3, Hey b 8, Hey b 9, Hey b 10 and Hey b 11; grasses, such as *Phleum pretense* allergens Phl p I, Phl p 2, Phl p 4, Phl p Sa, Phlp 5, Phlp 6, Phlp 7, Phl p 11, and Phl p 12; weeds, such as *Parietaria Judaica* allergen Par j 2.01011; and *Artemisia vulgaris* allergens Art v I and Art v 3; Mites, such as *Dermatophagoides pteronyssinus* allergens Der p I, Der p 2, Der p 5, Der p 7, Der p 8, and Der p 10; *Tyrophagu putrescentiae* allergen Tyr p 2; *Lepidoglyphus destructor* allergens Lep d 2.01 and Lep d 13; and *Euroglyphus maynei* allergen Eur m 2.0101; animals, such as cats, for example *Felis domesticus* allergen Fel d I; *Penaeus aztecus* allergen Pen a I; *Cyprinus carpo* allergen Cyp c I; and albumin from cat, dog, cattle, mouse, rat, pig, sheep, chicken, rabbit, hamster, horse, pigeon, and guinea pig; Fungi, such as *Penicillium citrinum* allergens Pen c 3 and Pen c 19; *Penicillium notatum* allergen Penn13; *Aspergillus fumigatus* allergens Asp f I, Asp f3, Asp f4, Asp f6, Asp f7 and Asp f8; *Alternaria alternata* allergens Alt a I and Alt a 5; *Malassezia furfur* allergen Mal f I, Mal f 5, Mal f 6, Mal f 7, Mal f 8, and Mal f 9; insects, such as *Blatella germanica* allergens Bla g 2, Bla g 4, and Bla g 5; *Apis mellifera* allergens Api m 2 and Api m I; *Vespula vulgaris* allergen Ves v 5; *Vespula germanica* allergen Ves g 5; and *Polstes annularis* allergen Pol a 5; food, such as *Malus domestica* allergens Mal d I and Mal d 2; *Apium graveolens* allergens Api g I and Api g 1.0201; *Daucus carota* allergen Dau c I; and *Arachis hypogaea* allergens Ara h 2 and Ara h 5 and the like. In some embodiments, an allergen or portion thereof is part of a functionalized surface or electrode, thus a disclosed functionalized surface can be used to measure the presence and concentration of antibodies in a sample that specifically bind an allergen. In some embodiments, an antibody that specifically binds an allergen or portion thereof is part of a disclosed functionalized surface or electrode, thus a disclosed functionalized electrode can be used to measure the presence and concentration of an allergen.

"Antibody" collectively refers to immunoglobulins or immunoglobulin-like molecules (including by way of example and without limitation, IgA, IgD, IgE, IgG and IgM, combinations thereof), and similar molecules produced during an immune response in any chordate such as a vertebrate, for example, in mammals such as humans, goats, rabbits and mice and fragments thereof that specifically bind to a molecule of interest (or a group of highly similar molecules of interest) to the substantial exclusion of binding to other molecules. An "antibody" typically comprises a polypeptide ligand having at least a light chain or heavy chain immunoglobulin variable region that specifically recognizes and binds an epitope of an antigen. Exemplary antibodies include polyclonal and monoclonal antibodies.

The term antibody also includes paratope sequences that are able to bind other analytes.

Immunoglobulins are composed of a heavy and a light chain, each of which has a variable region, termed the variable heavy (VH) region and the variable light (VL) region. Together, the VH region and the VL region are responsible for binding the antigen recognized by the immunoglobulin. Exemplary immunoglobulin fragments include, without limitation, proteolytic immunoglobulin fragments (such as F(ab')2 fragments, Fab' fragments, Fab'-SH fragments and Fab fragments as are known in the art), recombinant immunoglobulin fragments (such as sFv fragments, dsFv fragments, bispecific sFv fragments, bispecific dsFv fragments, F(ab)'2 fragments), single chain Fv proteins ("scFv"), and disulfide stabilized Fv proteins ("dsFv"). Other examples of antibodies include diabodies, and triabodies (as are known in the art), and camelid antibodies. "Antibody" also includes genetically engineered molecules, such as chimeric antibody. "Antibody" also includes genetically engineered molecules, such as chimeric antibodies (for example, humanized murine antibodies), and heteroconjugate antibodies (such as, bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., (1991) Sequences of Proteins of Immunological Interest, 5th Edition, U.S. Department of Health and Human Services, Public Health Service, National Institutes of Health, Bethesda, Md. Publication No. 91-3242) which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space, for example to hold the CDRs in an appropriate orientation for antigen binding.

The CDRs are primarily responsible for binding to an epitope of an antigen. The CDRs of each chain are typically referred to as CDRI, CDR2 and CDR3, numbered sequentially starting from the N terminus and are also typically identified by the chain in which the particular CDR is located. Thus, a VH CDR3 is located in the variable domain of the heavy chain of the antibody in which it is found, whereas a VL CDRI is the CDRI from the variable domain of the light chain of the antibody in which it is found.

A "monoclonal antibody" is an antibody produced by a single clone of B-lymphocytes or by a cell into which the light and heavy chain genes of a single antibody have been transfected or transduced. Monoclonal antibodies are produced by methods known to those of skill in the art, for instance by making hybrid antibody-forming cells from a fusion of myeloma cells with immune spleen cells. These fused cells and their progeny are termed "hybridomas". Monoclonal antibodies include humanized monoclonal antibodies. [0048] A "humanized" immunoglobulin, is an immunoglobulin including a human framework region and one or more CDRs from a non-human (such as a mouse, rat or synthetic) immunoglobulin. The non-human immunoglobulin providing the CDRs is termed a "donor", and the human immunoglobulin providing the framework is termed an "acceptor". In one embodiment, all the CDRs are from the donor immunoglobulin in a humanized immunoglobulin. Constant regions need not be present, but if they are, they must be substantially identical to human immunoglobulin constant regions, for example at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example see U.S. Pat. No. 5,585,089).

In some embodiments, an antibody specifically binds an antigen of interest, such as an antigen that is part of a disclosed functionalized electrode, for example covalently bonded to a thiol or dithiol compound or a functionalized thiol or dithiol compound that itself is bonded to an electrode surface. In some embodiments, an antibody specific for an antigen of interest is part of a disclosed functionalized electrode for example covalently bonded to a thiol or dithiol compound or a functionalized thiol or dithiol compound that itself is bonded to an electrode surface. In some embodiments, an antibody is part of a detection reagent that includes an enzyme.

Antigen: A compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other antigens known in the art.

In some embodiments, an antigen is a ligand for an antibody of interest, such as an antibody that is part of a disclosed functionalized electrode, for example covalently bonded to a thiol or dithiol compound or a functionalized thiol or dithiol compound that itself is bonded to an electrode surface. In some embodiments, an antigen of interest is part of a disclosed functionalized electrode, for example covalently bonded to a thiol or dithiol compound or a functionalized thiol or dithiol compound that itself is bonded to an electrode surface.

Aptamer: Small nucleic acid and peptide molecules that bind a specific target molecule, such as a target biomolecule, for example an analyte, such as a target analyte. In some examples an aptamer is part of a disclosed modified surface such as a functionalized electrode.

Bacterial pathogen: A bacteria that causes disease (pathogenic bacteria). Examples of pathogenic bacteria from which antigens for use in the disclosed functionalized electrodes can be derived include without limitation any one or more of (or any combination of) *Acinetobacter baumanii, Actinobacillus* sp., Actinomycetes, *Actinomyces* sp. (such as *Actinomyces israelii* and *Actinomyces naeslundii*), *Aeromonas* sp. (such as *Aeromonas hydrophila, Aeromonas veronii* biovar *sobria* (*Aeromonas sobria*), and *Aeromonas caviae*), *Anaplasma phagocytophilum, Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis,* and *Bacillus stearothermophilus*), *Bacteroides* sp. (such as *Bacteroides Bartonella* sp. (such as *Bartonella bacilliformis* and *Bartonella henselae, Bifidobacterium* sp., *Bordetella* sp. (such as *Bordetella pertussis, Bordetella parapertussis,* and *Bordetella bronchiseptica*), *Borrelia* sp. (such as *Borrelia recurrentis,* and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium*), *Clostridium* sp. (such as *Clostridium perfringens, Clostridium docile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus*), *Helicobacter* sp. (such as *Helicobacter pylori, Helicobacter cinaedi* and *Helicobacter fennelliae*), *Eingella kingii, Elebsiella* sp. (such as *Elebsiella pneumoniae, Elebsiella granulomatis* and *Elebsiella oxytoca*), *Lactobacillus* sp., *Listeria monocytogenes, Leptospira interrogans, Legionella pneumophila, Leptospira interrogans, Peptostreptococcus* sp., *Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium intracellulare, Mycobacterium avium, Mycobacterium bovis,* and *Mycobacterium marinum*), *Mycoplasm* sp. (such as *Mycoplasma pneumoniae, Mycoplasma hominis,* and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Pre-* votella melami nogenica, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella cholerasuis* and *Salmonella typhimurium*), *Serratia* sp. (such as *Serratia marescens* and *Serratia liquifaciens*), *Shigella* sp. (such as *Shigella dysenteriae*, *Shigella flexneri*, *Shigella boydii* and *Shigella sonnei*), *Staphylococcus* sp. (such as *Staphylococcus aureus*, *Staphylococcus epidermidis*, *Staphylococcus hemolyticus*, *Staphylococcus saprophyticus*), *Streptococcus* sp. (such as *Streptococcus pneumoniae* (for example chloramphenicol resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), *Spirillum minus*, *Streptobacillus moniliformi*, *Treponema* sp. (such as *Treponema carateum*, *Treponema petenue*, *Treponema pallidum* and *Treponema endemicum*, *Tropheryma whippelii*, *Ureaplasma urealyticum*, *Veillonella* sp., *Vibrio* sp. (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fiuvialis*, *Vibrio metchnilrovii*, *Vibrio damsela* and *Vibrio furnisii*), *Yersinia* sp. (such as *Yersinia enterocolitica*, *Yersinia pestis*, and *Yersinia pseudotuberculosis*) and *Xanthomonas maltophilia* among others.

Bacterial antigens suitable for use in the disclosed methods and compositions include proteins, polysaccharides, lipopolysaccharides, and outer membrane vesicles which may be isolated, purified or derived from a bacterium. In addition, bacterial antigens include bacterial lysates and inactivated bacteria formulations. Bacteria antigens can be produced by recombinant expression. Bacterial antigens preferably include epitopes which are exposed on the surface of the bacteria during at least one stage of its life cycle. Bacterial antigens include but are not limited to antigens derived from one or more of the bacteria set forth above as well as the specific antigens examples identified below.

*Neiserria gonorrhoeae* antigens include Por (or porn) protein, such as PorB (see, e.g., Zhu et al. (2004) Vaccine 22:660-669), a transferring binding protein, such as TbpA and TbpB (see, e.g., Price et al. (2004) Infect. Immun. 71(1):277-283), an opacity protein (such as Opa), a reduction-modifiable protein (Rmp), and outer membrane vesicle (OMV) preparations (see, e.g., Plante et al. (2000) J. Infect. Dis. 182:848-855); WO 99/24578; WO 99/36544; WO 99/57280; and WO 02/079243, all of which are incorporated by reference).

*Chlamydia trachomatis* antigens include antigens derived from serotypes A, B, Ba and C (agents of trachoma, a cause of blindness), serotypes Li, L3 (associated with Lymphogranuloma venereum), and serotypes, D-K. *Chlamydia trachomas* antigens also include antigens identified in WO 00/37494; WO 03/049762; WO 03/068811; and WO 05/002619 (all of which are incorporated by reference), including PepA (CT045), LcrE (CT089), Art (CT381),DnaK (CT396), CT398, OmpH-like (CT242), L7/L12 (CT316), OmcA (CT444), AtosS (CT467), CT547, Eno (CT587), HrtA (CT823), MurG (CT761), CT396 and CT761, and specific combinations of these antigens.

*Treponema pallidum* (Syphilis) antigens include TmpA antigen.

The compositions of the disclosure can include one or more antigens derived from a sexually transmitted disease (STD). Such antigens can provide for prophylactis or therapy for STDs such as *chlamydia*, genital herpes, hepatitis (such as HCV), genital warts, gonorrhea, syphilis and/or chancroid (see WO 00/15255, which is incorporated by reference). Antigens may be derived from one or more viral or bacterial STDs. Viral STD antigens for use in the invention may be derived from, for example, HIV, herpes simplex virus (HSV-I and HSV-2), human papillomavirus (HPV), and hepatitis (HCV). Bacterial STD antigens for use in the invention may be derived from, for example, *Neiserria gonorrhoeae*, *Chlamydia trachomatis*, *Treponema pallidum*, *Haemophilus ducreyi*, *E. coli*, and *Streptococcus agalactiae*.

In some embodiments, a disclosed functionalized surface or electrode includes one or more antigens derived from one or more of the organisms listed above. In some embodiments, an antibody that specifically binds antigens derived from one or more of the organisms listed above is part of a disclosed functionalized electrode, and thus in some examples can be used to detect such antigens in a sample, for example to diagnose a particular bacterial infection.

Binding affinity: Affinity of a specific binding agent for its target, such as an antibody for an antigen, for example an antibody for a target analyte, such as a target analyte. In one embodiment, affinity is calculated by a modification of the Scatchard method described by Frankel et al., *Mol. Immunol.*, 16:101-106, 1979. In another embodiment, binding affinity is measured by a specific binding agent receptor dissociation rate. In yet another embodiment, a high binding affinity is measured by a competition radioimmunoassay. In several examples, a high binding affinity ($K_D$) is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$ or at least about $5.0 \times 10^{-8}$ M.

Biomolecule: Any molecule that was derived from biological system, including but not limited to, a synthetic or naturally occurring protein, glycoprotein, lipoprotein, amino acid, nucleoside, nucleotide, nucleic acid, oligonucleotide, DNA, PNA, RNA, carbohydrate, sugar, lipid, fatty acid, hapten, antibiotics, vitamins, enterotoxins and the like. In some examples, a biomolecule is a target analyte for which the presence and or concentration or amount can be determined. In some embodiments a biomolecule is covalently bonded to a thiol or dithiol compound, and/or a cross-linker, such as a thiol or dithiol compound that is part of a disclosed functionalized metal surface, in particular an electrode.

Chemokines: Proteins classified according to shared structural characteristics such as small size (approximately 8-10 kilodaltons (kDa) in mass) and the presence of four cysteine residues in conserved locations that are key to forming their 3-dimensional shape. These proteins exert their biological effects by interacting with G protein-linked trans-membrane receptors called chemokine receptors that are selectively found at the surfaces of their target cells. Chemokines bind to chemokine receptors and thus are chemokine receptor ligands.

Examples of chemokines include the CCL chemokines such as CCL1, CCL2, CCL3, CCL4, CCLS, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27 and CCL28; CXCL chemokines such as CXCL1, CXCL2, CXCL3, CXCL4, CXCLS, CXCL6, CXCL7, CXCL8, CXCL9, CXCL10, CXCL11, CXCL12, CXCL13, CXCL14, CXCL15, CXCL16 and CXCL17; XCL chemokines such as XCL1 and XCL2; and CX3CL chemokines such as CX3CL1. In some embodiments, a chemokine or portion thereof is part of a disclosed functionalized electrode. In some embodiments, an antibody that specifically binds a chemokine or portion thereof is part of a functionalized electrode, and thus in some examples can be used to detect such chemokines in a sample.

Conjugating, joining, bonding or linking: Chemically coupling a first unit to a second unit. This includes, but is not limited to, covalently bonding one molecule to another molecule, non-covalently bonding one molecule to another (e.g., electro-statically bonding), non-covalently bonding one molecule to another molecule by hydrogen bonding, non-covalently bonding one molecule to another molecule by van der Waals forces, and any and all combinations of such couplings. In some embodiments a ligand for a target analyte is covalently bonded to a thiol or dithiol compound, and/or a cross-linker.

Contacting: Placement in direct physical association including both in solid or liquid form.

Control: A reference standard. In some examples, a control can be a known value indicative of a known concentration or amount of an analyte, such as a target analyte for example a biomolecule of interest. In some examples a control, or a set of controls of known concentration or amount, can be used to calibrate a functionalized electrode.

A difference between a test sample and a control can be an increase or conversely a decrease. The difference can be a qualitative difference or a quantitative difference, for example a statistically significant difference. In some examples, a difference is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Complex (complexed): Two proteins, or fragments or derivatives thereof, one protein (or fragment or derivative) and a non-protein compound, molecule or any two or more compounds are said to form a complex when they measurably associate with each other in a specific manner. In some examples, a complex is the complex formed between a functionalized electrode and a target analyte.

Covalent bond: An interatomic bond between two atoms, characterized by the sharing of one or more pairs of electrons by the atoms. The terms "covalently bound" or "covalently linked" refer to making two separate molecules into one contiguous molecule, for example ligand specific for a target analyte and a thiol or dithiol compound can be covalently linked (such as directly or indirectly through a linker).

Cross-linker: A homo- or hetero-multifunctional reagent with at least two non-identical groups, which are reactive to at least one functional group present in biomolecules, such as sulfhydryl groups, in a photoreaction and another functional group which forms a covalent bond to the metallic surface. Both functional groups are as a rule separated from each other by a Spacer group. In some examples, a protein cross-linker is sulfhydryl reactive, meaning it is capable of forming a covalent bond with a sulfhydryl group, such as an sulfhydryl group present in a biomolecule, for example a sulfhydryl group present on a cysteine residue, or for example a sulfhydryl group introduced by reacting an amine group with an agent which carries a protected sulfhydryl group followed by deprotection.

Cytokine: A generic name for a diverse group of soluble proteins and peptides that act as humoral regulators at nano- to pico-molar concentrations and which, either under normal or pathological conditions, modulate the functional activities of individual cells and tissues. These proteins also mediate interactions between cells directly and regulate processes taking place in the extracellular environment. Cytokines include both naturally occurring peptides and variants that retain full or partial biological activity. Cytokines bind to cytokine receptors and thus are cytokine receptor ligands.

Examples of cytokines include interleukins, such as IL-1 a, IL-3, IL-4, IL-5, IL-6, IL-7, IL-8, IL-10 and IL-12; interferons, such as IFN-a, IFN-(3 and IFN-γ; tumor necrosis factors, such as TNF-a and TNF-(3 macrophage; inflammatory proteins, such as MIP-1 a and MIP-1 3; and transforming growth factors, such as TGF-(3. In some embodiments, a cytokine or portion thereof is part of a disclosed functionalized electrode. In some embodiments, an antibody that specifically binds a cytokine or portion thereof is part of a disclosed functionalized electrode, thus the presence of a cytokine in a sample can be determined using a disclosed functionalized electrode.

Cyclic voltammetry: An electrochemical technique that can be used to obtain information about the redox potential of analyte solutions or enzyme substrate pairs, for example to select an enzyme substrate pair for inclusion in a disclosed biosensor. The voltage is swept between two values at a fixed rate, however, when the voltage reaches V2 the scan is reversed and the voltage is swept back to V1. The voltage is measured between a reference electrode and the working electrode, while the current is measured between the working electrode and the counter electrode. The obtained measurements are plotted as current vs. voltage, also known as a voltammogram. As the voltage is increased toward the electrochemical reduction potential of the analyte, the current will also increase. With increasing voltage toward V2 past this reduction potential, the current decreases, having formed a peak, since the oxidation potential has been exceeded. As the voltage is reversed to complete the scan toward V1, the reaction will begin to reoxidize the product from the initial reaction. This produces an increase in current of opposite polarity as compared to the forward scan, but again decreases having formed a second peak as the voltage scan continues toward V1. The reverse scan also provides information about the reversibility of a reaction at a given scan rate. The shape of the voltammogram for a given compound depends not only on the scan rate and the electrode surface, which is different after each adsorption step, but can also depend on the catalyst concentration.

Detect: To determine if an agent (such as a signal or target analyte) is present or absent. In some examples, this can further include quantification. In some examples, an electromagnetic signal is used to detect the presence, amount or concentration of an agent, such as an analyte. In some examples, the detection is indirect, for example using an enzyme that catalyzes the production of a detectable signal when an analyte is present. In other examples, the signal is reduced when the analyte is present, such that increasing concentration of an analyte gives a decrease in signal.

Dithiol group: A terminal group of a cross-linker which exhibits two thiol or sulfhydryl groups as a rule separated by a $C_{1-5}$ alkylenediyl group. Most preferred are those dithiols, which can be obtained by reduction of a liponic acid derivative.

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Electromagnetic radiation: A series of electromagnetic waves that are propagated by simultaneous periodic variations of electric and magnetic field intensity, and that includes radio waves, infrared, visible light, ultraviolet (UV) light, X-rays and gamma rays. In particular examples, electromagnetic is in the form of electrons, which can be detected as a change in current in an electrode, for example the functionalized metal surfaces disclosed herein.

Fungal pathogen: A fungus that causes disease. Examples of fungal pathogens for use in accordance with the disclosed methods and compositions include without limitation any one or more of (or any combination of) *Trichophyton rubrum, T mentagrophytes, Epidermophyton floccosum, Microsporum canis, Pityrosporum orbiculare* (*Malassezia furfur*), *Candida* sp. (such as *Candida albicans*), *Aspergillus* sp. (such as *Aspergillus fumigatus, Aspergillus flavus* and *Aspergillus clavatus*), *Cryptococcus* sp. (such as *Cryptococcus neoformans, Ciyptococcus gattii, Ciyptococcus laurentii* and *Ciyptococcus albidus*), *Histoplasma* sp. (such as *Histoplasma capsulatum*), *Pneumocystis* sp. (such as *Pneumocystis jirovecii*), and *Stachybotrys* (such as *Stachybotrys chartarum*). In some embodiments, a disclosed functionalized substrate or electrode includes one or more antigens derived from one or more of the organisms listed above. In some embodiments, an antibody that specifically binds antigens derived from one or more of the organisms listed above is part of a disclosed functionalized electrode, and thus in some examples can be used to detect such antigens in a sample, for example to diagnose a particular fungal infection or the presence of a fungus in an environmental sample.

Growth factor: Proteins capable of stimulating cellular proliferation and cellular differentiation. Examples of growth factors include transforming growth factor beta (TGF-(3), granulocyte-colony stimulating factor (G-CSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF-8), growth differentiation factor-9 (GDF-9), basic fibroblast growth factor (bFGF or FGF2), epidermal growth factor (EGF), hepatocyte growth factor (HGF) and the like. In some embodiments, a growth factor or portion thereof is part of a disclosed functionalized electrode. In some embodiments, an antibody that specifically binds a growth factor or portion thereof is part of a disclosed functionalized electrode and thus in some examples can be used to detect such growth factors in a sample.

Heterologous: With reference to a molecule, such as a linker, "heterologous" refers to molecules that are not normally associated with each other, for example as a single molecule. Thus, a "heterologous" linker is a linker attached to another molecule that the linker is usually not found in association with in nature, such as in a wild-type molecule.

High throughput technique: Through this process, one can rapidly identify analytes present in a sample or multiple samples. In certain examples, combining modern robotics, data processing and control software, liquid handling devices, and sensitive detectors, high throughput techniques allows the rapid detection and/or quantification of an analyte in a short period of time, for example using the assays and compositions disclosed herein.

Hormone: A classification of small molecules that carries a signal from one cell (or group of cells) to another. Examples of hormones include amine-tryptophans, such as melatonin (n-acetyl-5-methoxytryptamine) and serotonin; amine-tyrosines, such as thyroxine (thyroid hormone), tri-iodothyronine (thyroid hormone), epinephrine (adrenaline), norepinephrine (noradrenaline) and dopamine; peptide hormones, such as antimullerian hormone (mullerian inhibiting factor), adiponectin, adrenocorticotropic hormone (orticotropin), angiotensinogen and angiotensin, antidiuretic hormone (vasopressin, arginine vasopressin), atrial-natriuretic peptide atriopeptin), calcitonin, cholecystokinin, corticotropin-releasing hormone, erythropoietin, follicle-stimulating hormone, gastrin, ghrelin, glucagon, gonadotropin-releasing hormone, growth hormone-releasing hormone, human chorionic gonadotropin, human placental lactogen, growth hormone, inhibin, insulin, insulin-like growth factor (somatomedin), leptin, luteinizing hormone, melanocyte stimulating hormone, oxytocin, parathyroid hormone, prolactin, relaxin, secretin, somatostatin, thrombopoietin, thyroid-stimulating hormone and thyrotropin-releasing hormone; steroids, such as cortisol, aldosterone, testosterone, dehydroepiandrosterone, androstenedione, dihydrotestosterone, estradiol, estrone, estriol, progesterone and calcitriol (Vitamin d3); and eicosanoids, such as prostaglandins, leukotrienes, prostacyclin and thromboxane, among others. In some embodiments, a hormone or portion thereof is part of a disclosed functionalized electrode. In some embodiments, an antibody that specifically binds a hormone or portion thereof is part of disclosed functionalized electrode. Thus in some examples the disclosed functionalized electrodes can be used to detect such hormones and the pre-cursors and analogoues thereof.

Isolated: An "isolated" biological component (such as a biomolecule) has been substantially separated or purified away from other components in a mixture.

Ligand: Any molecule which specifically binds an analyte of interest (for example a target analyte), such as an antibody, protein, peptide or a small molecule (for example a molecule with a molecular mass less than 10 kilodaltons, (kDa) that specifically binds an analyte, such as a target analyte).

Linker or cross-linker: A compound or moiety that acts as a molecular bridge to operably link two different molecules, wherein one portion of the linker is operably linked to a first molecule and wherein another portion of the linker is operably linked to a second molecule. The two different molecules can be linked to the linker in a stepwise manner. There is no particular size or content limitations for the linker so long as it can fulfil its purpose as a molecular bridge. Linkers are known to those skilled in the art to include, but are not limited to, chemical chains, chemical compounds, carbohydrate chains, peptides, haptens and the like. The linkers can include, but are not limited to, homobifunctional linkers and heterobifunctional linkers. Heterobifunctional linkers, well known to those skilled in the art, contain one end having a first reactive functionality to specifically link a first molecule and an opposite end having a second reactive functionality to specifically link to a second molecule. Depending on such factors as the molecules to be linked and the conditions in which the method of detection is performed, the linker can vary in length and composition for optimizing such properties as flexibility, stability and resistance to certain chemical and/or temperature parameters.

Nucleic acid: A polymer composed of nucleotide units (ribonucleotides, deoxyribonucleotides, related naturally occurring structural variants and synthetic non-naturally occurring analogues thereof or combinations thereof) linked via phosphodiester bonds, related naturally occurring structural variants and synthetic non-naturally occurring analogues thereof. Thus, the term includes nucleotide polymers in which the nucleotides and the linkages between them include non-naturally occurring synthetic analogs, such as, for example and without limitation, phosphorothiolates, phosphoramidates, methyl phosphonates, chiral-methyl phosphonates, 2-O-methyl ribonucleotides, peptide-nucleic acids (PNAs) and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, for example a "recombinant polypeptide." A recombinant nucleic acid may serve a non-coding function (for example a promoter, origin of replication, ribosome-binding site, etc.) as well.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA and TFASTA in the Wisconsin Genetics Software Package, Genetics Computer Group, 575 Science Dr., Madison, Wis.) or by manual alignment and visual inspection (see, for example, *Current Protocols in Molecular Biology* (Ausubel et al., eds 1995 supplement)).

Nucleotide: The fundamental unit of nucleic acid molecules. A nucleotide includes a nitrogen-containing base attached to a pentose monosaccharide with one, two or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetyl-cytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-meth-ylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxy-acetic acid methyl ester, uracil-5-oxyacetic acid, 5-methyl-2-thiouracil, 3-(3-amino-3-N-2-carb oxypropyl)uracil and 2,6-di aminopurine 2'-deoxyguanosine amongst others.

Examples of modified sugar moieties, which may be used to modify nucleotides at any position on its structure, include, but are not limited to arabinose, 2-fluoroarabinose, xylose and hexose or a modified component of the phosphate backbone, such as phosphorothioate, a phosphorodithioate, a phosphoramidothioate, a phosphoramidate, a phosphordiamidate, a methylphosphonate or an alkyl phosphotriester or analog thereof.

Neuropeptide: Peptides released by neurons in the mammalian brain that specifically bind a neuropeptide receptor. Examples of neuropeptides include a-melanocyte-stimulating hormone (a-MSH), galanin-like peptide, a cocaine-andamphetamine-regulated transcript (CART), neuropeptide Y, agouti-related peptide (AGRP), β-endorphin, dynorphin, enkephalin, galanin, ghrelin, growth-hormone releasing hormone, neurotensin, neuromedin U, somatostatin, galanin, enkephalin cholecystokinin, vasoactive intestinal polypeptide (VIP) and substance P among others. In some embodiments, a neuropeptide or portion thereof is part of a disclosed functionalized electrode. In some embodiments, an antibody that specifically binds a neuropeptide or portion thereof is part of a functionalize electrode, and thus in some examples can be used to detect such peptides in a sample.

Oligonucleotide: A linear polynucleotide sequence of up to about 100 nucleotide bases in length.

Parasite: An organism that lives inside humans or other organisms acting as hosts (for the parasite). Parasites are dependent on their hosts for at least part of their life cycle. Parasites are harmful to humans because they consume needed food, eat away body tissues and cells, and eliminate toxic waste, which makes people sick. Examples of parasites for use in accordance with the disclosed methods and compositions include without limitation any one or more of (or any combination of) Malaria (*Plasmodium falciparum, P vivax, P malariae*), Schistosomes, Trypanosomes, *Leishmania*, Filarial nematodes, Trichomoniasis, Sarcosporidiasis, *Taenia* (*T. saginata, T. solium*), *Toxoplasma gondii*, Trichinelosis (*Trichinella spiralis*) or Coccidiosis (*Eimedia* species). Thus in some embodiments, a disclosed functionalized electrode includes one or more antigens derived from one or more of the organisms listed above. In some embodiments, an antibody that specifically binds antigens derived from one or more of the organisms listed above is part of a disclosed functionalized electrode. Thus in some examples a disclosed functionalized electrode can be used to detect such parasites in a sample, for example to diagnose a particular parasitic infection or the presence of parasites in an environmental sample.

Photo-initiator: An organic molecule or group, which is cleaved into separate radical groups upon irradiation with UV light. Preferred are such molecules or groups which derive from α-hydroxy-, α-alkoxy- or α-amino-arylketons, preferably they exhibit a 1-benzoyl-1-methyl-ethanol moiety; most preferred photo-initiators are 2-hydroxy-4'-(2-hydroxyethoxy)-2-methylpropiophenone and 2,2-dimethoxy-2-phenylphenone. In "the presence of a photo-initiator" means that a photo-initiator is either added in the form of a solution prior to the photoreaction or has been previously attached to the metal surface as disclosed for example by U.S. Pat. No. 8,580,571.

Polypeptide: A polymer in which the monomers are amino acid residues, which are joined together through amide bonds. When the amino acids are a-amino acids, either the L-optical isomer or the D-optical isomer can be used. The terms "polypeptide" or "protein" as used herein are intended to encompass any amino acid sequence and include modified sequences such as glycoproteins. "Polypeptide" covers naturally occurring proteins, as well as those which are recombinantly or synthetically produced. "Residue" or "amino acid residue" includes an amino acid that is incorporated into a protein, polypeptide, or peptide.

Purified: The term "purified" does not require absolute purity; rather, it is intended as a relative term. Thus, for example, a purified peptide, protein, conjugate, or other compound is one that is isolated in whole or in part from proteins or other constituents of a mixture. Generally, substantially purified peptides, proteins, conjugates, or other active compounds for use within the disclosure comprise more than 80% of all macromolecular species present in a preparation prior to admixture or formulation of the peptide, protein, conjugate or other active compound with a pharmaceutical carrier, excipient, buffer, absorption enhancing agent, stabilizer, preservative, adjuvant or other co-ingredient. More typically, the peptide, protein, conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Quantitating: Determining or measuring a quantity (such as a relative quantity) of a molecule or the activity of a molecule, such as the quantity of analyte, such as a target analyte present in a sample.

Sample: A material to be analysed. In one embodiment, a sample is a biological sample. In another embodiment, a sample is an environmental sample, such as soil, sediment water, or air. Environmental samples can be obtained from an industrial source, such as a farm, waste stream, or water source. A biological sample is one that includes biological materials (such as nucleic acid and proteins). In some examples, a biological sample is obtained from an organism or a part thereof, such as an animal. In particular embodiments, the biological sample is obtained from an animal subject, such as a human subject. A biological sample can be any solid or fluid sample obtained from, excreted by or secreted by any living organism, including without limitation multicellular organisms (such as animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a cell lysate, for example a cell lysate obtained from a tumor of a subject.

Spacer group: A group within the cross-linker, which separates the two terminal reactive groups, one of which binds to the metal surface and the other to a sulfhydryl group of the biomolecule upon irradiation. The Spacer group is preferably a $C_5$-30 alkylene-di-1,ω-yl group, wherein one or more non-adjacent $CH_2$ groups may be replaced each independently by a group selected from O, S, NH, NR, NR—CO, CO—NR, O—CO and CO—O, wherein R represents hydrogen or $C_{1-6}$ alkyl. Polyethyleneglycol (PEG) groups are preferred components of such Spacer groups.

Specific binding agent: An agent that binds substantially only to a defined target. Thus, an antigen binding agent, such as an antibody that is specific for an antigen is an agent that binds substantially to a specific antigen or fragment thereof. In some examples, the specific binding agent is a monoclonal or polyclonal antibody that specifically binds a specific antigen or antigenic fragment thereof, such as a target analyte. In other examples, the specific binding agent is an antigen that specifically binds to an antibody specific for the antigen. In some examples, a specific binding agent is conjugated to an enzyme, such as an enzyme that catalyzes the reaction of an enzyme Substrate into an electroactive product.

Subject: Includes both human and veterinary subjects, for example, humans, non-human primates, dogs, cats, horses, swine, and cows, and further subjects of the field of food production such as chicken or fishes such as salmon, tuna or trout. Other important subjects in the field of food production are plant materials.

Substrate: A molecule that is acted upon by an enzyme. A substrate binds with the enzyme's active site, and an enzyme-substrate complex is formed. In some examples an enzyme substrate is converted to an electroactive product by an enzyme.

Thiol: An organosulfur compound that contains a sulfur-hydrogen bond or sulfhydryl group (S—H). Thiols are the sulfur analogue of an alcohol. The S—H functional group can be referred to as either a thiol group or a sulfhydryl group. Thiols have the general chemical formula R—S—H. In some examples, the S—H group can react with and thereby bond to a surface, such as an electrically conductive surface.

Tumor antigen: A tumor antigen is an antigen produced by tumor cells that can stimulate tumor-specific T-cell immune responses. Exemplary tumor antigens include, but are not limited to, RAGE-1, tyrosinase, MAGE-1, MAGE-2, NY-ESO-1, Melan-A/MART-1, glycoprotein (gp) 75, gp100, beta-catenin, preferentially expressed antigen of melanoma (PRAME), MUM-1, Wilms tumor (WT)-1, carcinoembryonic antigen (CEA), and PR-1. Additional tumor antigens are known in the art (for example see Novellino et al., *Cancer Immunol. Immunother.* 54(3):187-207, 2005) and are described below. Tumor antigens are also referred to as "cancer antigens." The tumor antigen can be any tumor-associated antigen, which are well known in the art and include, for example, carcinoembryonic antigen (CEA), (3-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, macrophage colony stimulating factor, prostase, prostate-specific antigen (PSA), PAP, NY-ESO-1, LAGE-la, p53, prostein, PSMA, Her2/neu, survivin and telomerase, prostate-carcinoma tumor antigen-1, MAGE, ELF2M, neutrophil elastase, ephrinB2, CD22, insulin growth factor (IGF)-I, IGF-II, IGF-I receptor and mesothelin.

In some embodiments, a tumor antigen or portion thereof is part of a disclosed functionalized electrode. In some embodiments, an antibody that specifically binds a tumor antigen or portion thereof is part of a functionalized electrode. Thus in some examples the disclosed functionalized electrodes can be used to detect such antigens in a sample, for example to diagnose a cancer.

Virus: A microscopic infectious organism that reproduces inside living cells. A virus consists essentially of a core of nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so. In some examples, a virus is a pathogen. Another form of viruses are prions.

Specific examples of viral pathogens for use in accordance with the disclosed methods and compositions include without limitation any one or more of (or any combination of); Arenaviruses (such as Guanarito virus, Lassa virus, Junin virus, Machupo virus and Sabia), Arteriviruses, Roniviruses, Astroviruses, Bunyaviruses (such as Crimean-Congo hemorrhagic fever virus and Hantavirus), Barnaviruses, Birnaviruses, Bornaviruses (such as Borna disease virus), Bromoviruses, Caliciviruses, Chrysoviruses, Coronaviruses (such as Coronavirus and SARS), Cystoviruses, Closteroviruses, Comoviruses, Dicistroviruses, Flaviruses (such as Yellow fever virus, West Nile virus, Hepatitis C virus, and Dengue fever virus), Filoviruses (such as Ebola virus and Marburg virus), Flexiviruses, Hepeviruses (such as Hepatitis E virus), human adenoviruses (such as human adenovirus A-F), human astroviruses, human BK polyomaviruses, human bocaviruses, human coronavirus (such as a human coronavirus HKU1, NL63, and 0C43), human enteroviruses (such as human enterovirus A-D), human erythrovirus V9, human foamy viruses, human herpesviruses (such as human herpesvirus 1 (herpes simplex virus type 1), human herpes-virus 2 (herpes simplex virus type 2), human herpesvirus 3 (Varicella zoster virus), human herpesvirus 4 type 1 (Epstein-Barr virus type 1), human herpesvirus 4 type 2 (Epstein-Barr virus type 2), human herpesvirus 5 strain AD169, human herpesvirus 5 strain Merlin Strain, human herpesvirus 6A, human herpesvirus 6B, human herpesvirus 7, human herpes-virus 8 type M, human herpesvirus 8 type P and Human Cytomegalovirus), human immunodeficiency viruses (HIV) (such as HIV 1 and HIV 2), human metapneumoviruses, human papillomaviruses, human parainfluenza viruses (such as human parainfluenza virus 1-3), human parechoviruses, human parvoviruses (such as human parvovirus 4 and human parvovirus B19), human respiratory syncytial viruses, human rhinoviruses (such as human rhinovirus A and human rhinovirus B), human spumaretroviruses, human T-lymphotropic viruses (such as human T-lymphotropic virus 1 and human T-lymphotropic virus 2), Human polyoma viruses, Hypoviruses, Leviviruses, Luteoviruses, Lymphocytic choriomeningitis viruses (LCM), Marnaviruses, Narnaviruses, Nidovirales, Nodaviruses, Orthomyxoviruses (such as Influenza viruses), Partitiviruses, Paramyxoviruses (such as Measles virus and Mumps virus), Picornaviruses (such as Poliovirus, the common cold virus, and Hepatitis A virus), Potyviruses, Poxviruses (such as Variola and Cowpox), Sequiviruses, Reoviruses (such as Rotavirus), Rhabdoviruses (such as Rabies virus), Rhabdoviruses (such as Vesicular stomatitis virus, Tetraviruses, Togaviruses (such as Rubella virus and Ross River virus), Tombusviruses, Totiviruses, Tymoviruses, and Noroviruses among others.

Viral antigens may be from a Hepatitis C virus (HCV). HCV antigens may be selected from one or more of E1, E2, E1/E2, NS345 polyprotein, NS 345-core polyprotein, core, and/or peptides from the nonstructural regions (Houghton et al. (1991) *Hepatology* 14:381-388, which is incorporated by reference).

Viral antigens may be derived from a Human Herpes virus, such as Herpes Simplex Virus (HSV), Varicella-zoster virus (VZV), Epstein-Barr virus (EBV), or Cytomegalovirus (CMV). Human Herpes virus antigens may be selected from immediate early proteins, early proteins, and late proteins. HSV antigens may be derived from HSV-I or HSV-2 strains. HSV antigens may be selected from glycoproteins gB, gC, gD and gH, or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins. Exemplary herpes antigens include (GENBANK™ Accession No. in parentheses) those derived from human herpesvirus 1 (Herpes simplex virus type 1) (NC 001806), human herpesvirus 2 (Herpes simplex virus type 2) (NC 001798), human herpesvirus 3 (Varicella zoster virus) (NC 001348), human herpesvirus 4 type 1 (Epstein-Barr virus type 1) (NC 007605), human herpesvirus 4 type 2 (Epstein-Ban virus type 2) (NC 009334), human herpesvirus 5 strain AD169 (NC 001347), human herpesvirus 5 strain Merlin Strain (NC 006273), human herpesvirus 6A (NC 001664), human herpesvirus 6B (NC 000898), human herpesvirus 7 (NC 001716), human herpesvirus 8 type M (NC 003409), and human herpesvirus 8 type P (NC 009333).

Human Papilloma virus (HPV) antigens are known in the art and can be found for example in International Patent Publication No. WO96/19496, (incorporated by reference in its entirety) which discloses variants of HPV E6 and E7 proteins, particularly fusion proteins of E6/E7 with a deletion in both the E6 and E7 proteins. HPV L1 based antigens are disclosed in international Patent publication Nos. WO94/00152, WO94/20137, WO93/02184 and WO94/05792, all of which are incorporated by reference. Such an antigen can include the L1 antigen as a monomer, a capsomer or a virus like particle. Such particles may additionally comprise L2 proteins. Other HPV antigens are the early proteins, such as E7 or fusion proteins such as L2-E7. Exemplary HPV antigens include (GENBANK™ Accession No. in parentheses) those derived from human papillomavirus-1 (NC 001356), human papillomavirus-18 (NC 001357), human papillomavirus-2 (NC 001352), human papillomavirus-54 (NC 001676), human papillomavirus-61 (NC 001694), human papillomavirus-cand90 (NC 004104), human papillomavirus RTRX7 (NC 004761), human papillomavirus type 10 (NC 001576), human papillomavirus type 101 (NC 008189), human papillomavirus type 103 (NC 008188), human papillomavirus type 107 (NC 009239), human papillomavirus type 16 (NC 001526), human papillomavirus type 24 (NC 001683), human papillomavirus type 26 (NC 001583), human papillomavirus type 32 (NC 001586), human papillomavirus type 34 (NC 001587), human papillomavirus type 4 (NC 001457), human papillomavirus type 41 (NC 001354), human papillomavirus type 48 (NC 001690), human papillomavirus type 49 (NC 001591), human papillomavirus type 5 (NC 001531), human papillomavirus type 50 (NC 001691), human papillomavirus type 53 (NC 001593), human papillomavirus type 60 (NC 001693), human papillomavirus type 63 (NC 001458), human papillomavirus type 6b (NC 001355), human papillomavirus type 7 (NC 001595), human papillomavirus type 71 (NC 002644), human papillomavirus type 9 (NC 001596), human papillomavirus type 92 (NC 004500), and human papillomavirus type 96 (NC 005134).

Viral antigens may be derived from a Retrovirus, such as an Oncovirus, a Lentivirus or a Spumavirus. Oncovirus antigens may be derived from HTLV-I, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. Antigens for HIV are known in the art, for example HIV antigens may be selected from gag (p24gag and p55gag), env (gp160 and gp41), pol, tat, nef, rev vpu, miniproteins, (p55 gag and gp140v). HIV antigens may be derived from one or more of the following strains: HIVmb, HIV; HIVLAV, HIVLAI, HIVM N, HIV-1 CM235, HIV-1 US4. Examples of HIV antigens can be found in International Patent Publication Nos. WO 09/089, 568, WO 09/080,719, WO 08/099,284, and WO 00/15255, and U.S. Pat. Nos. 7,531,181 and 6,225,443, all of which are incorporated by reference. Exemplary HIV antigens include (GEN-BANK Accession No. in parentheses) those derived from human immunodeficiency virus 1 (NC 001802), human immunodeficiency virus 2 (NC 001722).

In some embodiments, a disclosed functionalized electrode includes one or more antigens derived from one or more of the viruses listed above. In some embodiments, an antibody that specifically binds antigens derived from one or more of the viruses listed above is part of a functionalized electrode. Thus in some examples the disclosed functionalized electrodes can be used to detect such viruses in a sample, for example to diagnose a viral infection or the presence of a virus in an environmental sample.

The general performance of electrochemical sensors is often determined by the surface architectures that connect the sensing element to the biological sample at the nanometer scale. Electrochemical biosensors have suffered from a lack of surface architectures allowing high enough sensitivity and unique identification of the response with the desired biochemical event.

Various prior attempts have been made to fashion biosensors out of long chain self-assembled monolayers (SAMs) because of the desirable characteristics of self-assembled monolayers, such as stability and resistance to non-specific biomolecule adsorption. However, electrochemical sensors based on long chain alkyls have suffered from limited applicability because of their low permeability to electron transfer (see e.g. Fragoso et al., *Anal. Chem.*, 80:2556-2563, 2008). In an attempt to overcome the perceived limitations present in long chain SAMs, Fragoso et al. turned to dithiols, which are believed to be less insulating. However, one of the advantages of using long chain SAMs is lost by turning to a less insulating monolayer, namely the loss of selectivity against non-specific electron transfer, which reduces the signal to noise of the sensor and therefore the sensitivity.

Another drawback to the use of SAMs is that they are ionic insulators, that is ions are not readily able to penetrate SAM in order to transfer electrons to and from the underlying electro-conductive material of an electrochemical sensor (see e.g. Boubour and Lennox, *Langmuir* 16:42224228, 2000). While the insulating properties of SAMs are desirable from the standpoint of limiting non-specific electron transfer, in the absence of selective ionic transfer for an analyte of interest, SAMs have limited use as components of electrochemical sensors.

As disclosed herein, the limitations present in previous attempts to create sensors from long chain thiol containing SAMs have been overcome by careful selection of thiol or dithiol compounds that retain their insulating properties toward non-specific electron transfer coupled with the selection of enzyme reaction products that are electro-active and capable of facilitating electron transfer through the monolayer to the electron conducting surface. Thus, disclosed herein it has been surprisingly found that functionalized electrodes can be formed that retain the beneficial insulating properties on SAMs such as to yield high signal to noise, in conjunction with high selectivity and sensitivity.

Kits are also provided herein. Kits for detecting analytes of interest contain a one or more of the disclosed biosensors. In some embodiments, a kit includes instructional materials disclosing means of detecting analytes of interest. The instructional materials may be written, in an electronic form (such as a computer diskette or compact disk) or may be visual (such as video files). The kits may also contain detection reagents and substrates that have electro-active reaction product. The kits may also include additional components to facilitate the particular application for which the kit is designed. Thus, for example, the kit may additionally contain buffers and other reagents routinely used for the practice of a particular method. Such kits and appropriate contents are well known to those of skill in the art. In some examples the kits contain controls, for examples control solutions containing a known amount or concentration of a target analyte, for example as a means calibrate the biosensors included in kits. The kit may contain components for automated assay testing, and automated data collection that would be useful in a rapid, point-of-care setting.

Preferred embodiments of the method according to this invention are those wherein:

(A) the cross-linker compound is a compound of formula (I), $$\text{HS—}(CH_2)_m\text{—CH(ZH)-SPACER-}(CH_2)_p\text{-A} \tag{I}$$

in which
m is an integer from 2 to 6, in particular 2 to 4,
A is selected from —CH=CH$_2$ and —C≡CH, in particular —CH=CH$_2$ and
Z is S or a single bond, in particular S,
SPACER is a group of formula $$-(CH_2)_n-(C=O)_x-Y-(CH_2CH_2-O)_y-\\-(CH_2)_r-(C=O)_v-X-$$

wherein
X and Y are each independently NH or O,
n is 0 or an integer from 1 to 10, in particular 2 to 6, most preferably 4,
x and v are each independently 0 or 1, in particular 1,
y is an integer from 1 to 20, in particular 4 to 18,
r and p are each independently selected from an integer from 1 to 6, in particular 1;

The polyethylene glycol group (PEG) —(CH$_2$CH$_2$—O)$_y$— contains either a defined number y of ethylene oxide units, in particular 4 to 18 units, most preferred 8 to 16 units, or contains an undefined number of ethylene oxide units with an average molecular mass of 0.5 to 10 kDa, in particular 2 to 8 kDa, most preferred about 5 kDa;

(B) the biomolecule is an antibody, an enzyme or nucleic acid, in particular a monoclonal antibody;

(C) the photo-initiator is a 1-benzoyl-1-methyl-ethanol derivative, in particular a 1-benzoyl-1-methyl-ethanol derivative, which is soluble in water, most preferably 2-hydroxy-4-(2-hydroxyethoxy)-2-metylpropiophenon;

(D) the irradiation is carried out at a wavelength $\lambda_{max}$ of 300 to 340 nm, in particular at about 320 nm.

Furthermore, the invention relates to the novel compounds of formula (I), preferred compounds of formula (I) are the following compounds of formula (IA):

$$\text{HS—}(CH_2)_m\text{—CH(SH)-SPACER-CH}_2\text{-A} \tag{IA}$$

in which A and SPACER have the meaning given for formula (I) and
m is an integer from 2 to 4, in particular 2,
The SPACER of formula (IA) is preferably a group of formula $$-(CH_2)_n-(C=O)-NH-(CH_2CH_2-O)_y-CH_2-\\(C=O)-NH-$$

wherein
n is 0 or an integer from 1 to 10, in particular 2 to 6, most preferably 4,
y is an integer from 1 to 20.

Most preferred are the compounds of formula (IB), which are obtainable from liponic acid, in particular from R-α-liponic acid by reduction of the —S—S— bond:

$$\text{HS—}(CH_2)_2\text{—CH(SH)—}(CH_2)_4\text{—}(C=O)\text{—NH—}\\(CH_2CH_2\text{—O})_y\text{—CH}_2\text{—}(C=O)\text{—NH—CH}_2\text{-A} \tag{IB},$$

wherein A and y have the meaning given for formula (I).

The preferred compounds of formulae (IA) and (B) can be synthesized according to the following Reaction Scheme I:

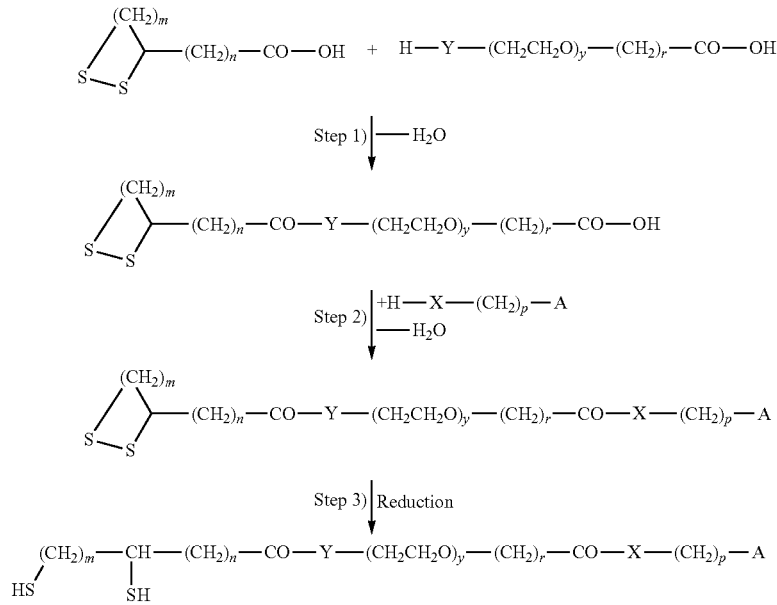

Reaction Scheme I

In Step 1) and Step 2) the corresponding acids are treated with an alcohol (Y or X=O) or an amine (Y or X=NH) under conditions of an esterification reaction or an amide forming reaction. Such reaction conditions are well known for the person skilled in the art. Either the acid is activated for example by treatment with N-hydroxysuccinimide (NETS) or thionyl chloride and/or the water formed during the reaction is irreversibly trapped by a dehydration agent.

Most preferred the acid is treated with the alcohol or amine in the presence of N-hydroxysuccinimide (NHS), sodium N-hydroxysulfosuccinimide, 1-hydroxybenzotriazol (HOBT), 1-hydroxy-7-azabenzotriazole (HOAT) or pentafluorphenol and dicyclohexylcarbodiimide (DCC) or 1-ethyl-3-(3-dimethylaminopropyl)carbodiimide (EDC).

In Step 3) the disulfide bond is reductively cleaved by treatment with an reduction agent, in particular with DTT (dithiothreitol), mercaptoethanol, tris(2-carboxyethyl)phosphine (TCEP) and/or DTE (dithioerythritol).

The preferred compounds of formula I, wherein X is S and v is 0 can be prepared according to the following Reaction Scheme II:

The protecting group PG is a group suitable to protect amino or hydroxyl groups. Such protecting groups and the methods of deprotection (Step 2)) are well known to the person skilled in the art, cp.: T. W. Green, P. G. M. Wuts, *Protective Groups in Organic Synthesis*, Wiley-Interscience, New York, 1999. Most preferred protecting groups for amino groups are for example: 9-Fluorenyl-methyl carbamate, (FMOC amino), t-butyl carbamate (BOC amino), benzyl carbamate, acetamide, trifluoroacetamide, benzylamine and tritylamine. Most preferred protecting groups for hydroxy groups are for example: methoxymethyl ether, tetrahydropyranyl ether, t-butyl ether, benzyl ether, trihydrocarbylsilylether such as t-butyldimethylsilyl ether or t-butyldiphenylsilyl ether.

The substitution reaction in Step 3) is as rule carried out in the presence of a base such as alkali metal hydroxide, preferably sodium hydroxide or potassium hydroxide, or an tertiary amine, preferably triethylamine or 2,2,6,6-tetrametylpiperidine.

Step 4 can be carried out analogously as described for Reaction Scheme 1, Step 3).

Accordingly, the new liponic acid derivatives of formula (II) are another subject matter of the present invention as intermediates for the preparation of the compounds of formulae (I), (IA) and (IB).

Reaction Scheme II

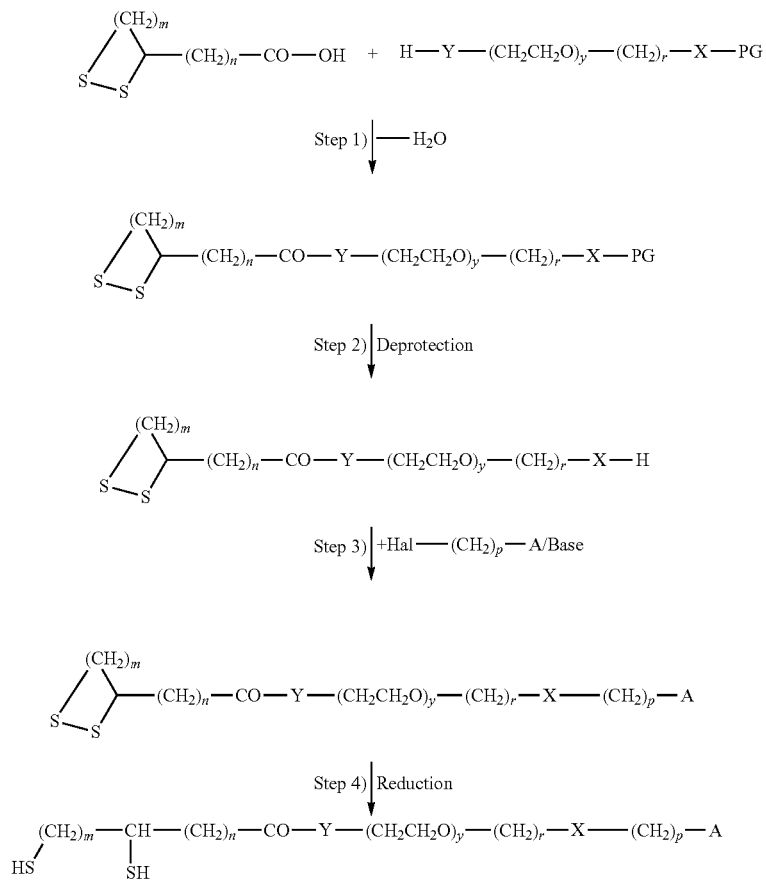

Most preferred are the compounds of formula (IIA),

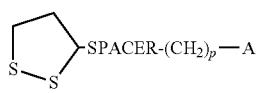

(IIA)

in particular the compounds of formula (IIA1),

(IIA1)

wherein SPACER, A and p have the meaning given for formula (I).

The present disclosure shall be illustrated by the following non-limiting Examples.

EXAMPLES

Abbreviations

AcOH acetic acid
approx. approximately
° C. degrees Celsius
DCC dicyclohexylcarbodiimide
DCM dichloromethane
DTT dithiothreitol
kDa kilodalton
MeCN acetonitrile
MeOH methanol
mL milliliter
mM millimolar
NHS N-hydroxysuccinimide
PEG-alkene methoxy poly (ethylene glycol) alkene
PEG-alkyne methoxy poly (ethylene glycol) alkyne
rpm revolutions per min
λ wavelength
TCEP tris(2-carboxyethyl)phosphine
TEA triethylamine
TFA trifluoroacetic acid

Example 1

Synthesis of SH-PEG-Alkene/-Alkyne Cross-Linker

For coupling of diagnostic biomolecules to microchips via PEG-alkene/-alkyne cross-linker PEG-alkene and PEG-alkyne molecules with average molecular weights of 800 Da and 5000 Da were synthesized. Furthermore, a SH-mPEG of 600 Da that was not functionalized with alkene or alkyne has been synthesized. This molecule can be used for dilution of the PEG-alkene/-alkyne cross-linker during coating of the metal surface in order to obtain a homogenous statistical distribution of functional groups on the chip surface.

Experimental

RP-HPLC—RP-HPLC analysis was performed on a Water alliance system equipped with an ELSD detector and a photo diode array detector. An XBRIDGE™ BEH300 4.6×250 mm 5 μm RP18 column was used. HPLC-H$_2$O (+0.1% TFA) and HPLC-MeCN (+0.1% TFA) were used as eluents in a gradient HPLC.

NMR—For NMR spectroscopy 30-60 mg of the analyte were solved in 600 μL CDCl3 and transferred to an NMR vial. The spectroscopy was performed using a Varian Mercury-400BB at (1H, 400 MHz; 13C, 100.6 MHz) or a Varian Mercury-300BB (1H, 300 MHz; 13C, 75.5 MHz). The chemical shift is indicated in ppm and was calibrated to the solvent signal.

MALDI-TOF-MS—MALDI-TOF-MS analysis was performed in the linear mode using an α-cyano-4-hydroxycinnamic acid (CHCA) matrix on an Axima confidence system (Shimadzu).

Stirring—A magnetic stir bar were added to all reaction mixtures and crystallization suspensions to stir them with a MR3001 K (Heidolph) magnetic stirrer.

Evaporation and Drying—Solvents were removed under reduced pressure to dryness with a Laborota 4000-efficient (Heidolph) rotary evaporator with a Vacuum Pump Unit PC510 (Vacuubrand) and a water bath temperature at 40° C. The same procedure is used for drying materials.

Chromatography—Chromatography was performed using 40-63 μm silica gel packed in glass columns with a mixture of different typical organic solvents. The fractions were collected manually and analyzed by TLC. The pure product containing fractions were combined and the solvent was removed under reduced pressure.

TLC—TLC analysis was carried out on TLC Silica gel 60 F254 aluminium sheets with different mixtures of typical organic solvents. An aqueous potassium permanganate solution was used as staining reagent.

Example 1.1

Synthesis of R-α-Lipoic Acid-PEG12-Allyl (B)

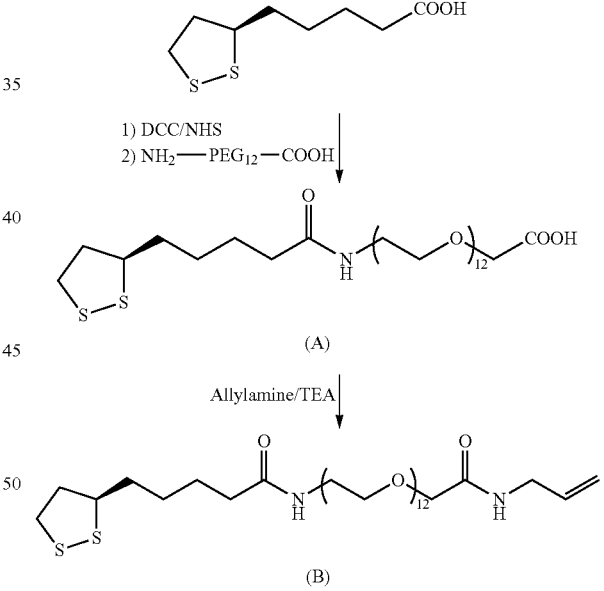

Step 1: To a solution of R-α-lipoic acid (668 mg, 3.24 mmol) in 40 mL DCM, DCC (1.00 g, 4.86 mmol) and NHS (599 mg, 4.86 mmol) were added and the resulting reaction mixture was stirred for 1 h at room temperature. The precipitated dicyclohexylurea was removed by filtration and washed twice with 10 mL DCM. To the resulting clear yellow reaction mixture NH$_2$-PEG12-COOH (2.00 g, 3.24 mmol) and TEA (900 μL, 6.48 mmol) were added. The reaction mixture was stirred for 2.5 h at room temperature. Subsequently the solvent was removed under reduced pressure. After purification of the resulting remains by chromatography (35 g silica gel (40-63 μm DCM/MeOH—98:

2→90:10, +0.1% AcOH) 1.99 g referring to a yield of 76% of the product (A) were obtained. According to RP-HPLC analysis the product contained approx. 3.3% lipoic acid and not identified impurity that amounted to 2.8%. The overall purity was approx. 94%.

Step 2: To a solution of the product ( ) obtained in Step 1 (1.20 g, 1.49 mmol) in 20 mL DCM, DCC (461 mg, 2.23 mmol) and NHS (257 mg, 2.23 mmol) were added and the resulting reaction mixture was stirred for 1 h at room temperature. The precipitated dicyclohexylurea was removed by filtration and washed twice with 5 mL DCM. To the resulting clear yellow reaction mixture allylamine (224 µL, 2.98 mmol) and TEA (415 µL, 2.99 mmol) were added. The reaction mixture was stirred for 17 h at room temperature and subsequently washed with 20 mL water. The organic phase was concentrated under reduced pressure and the resulting solid was purified by chromatography (15 g silica gel (40-63 µm DCM/MeOH—98:2→95:5). 796 mg referring to a yield of 63% of the product CES0594 were obtained. According to RP-HPLC analysis (FIG. 2) the product had a purity of >99%. The molecular weight and identity of (B) were confirmed by MALDI-MS and NMR.

Example 1.2

Synthesis of R-α-Lipoic-Acid-PEG12-Propargyl (C)

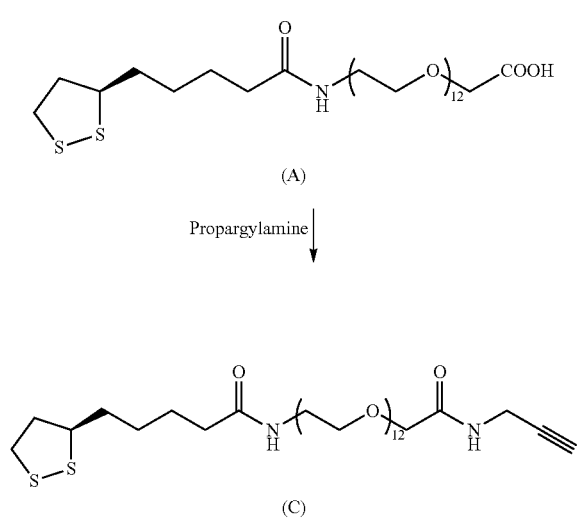

To a solution of product (A) as obtained in Step 1 of example 1.1. (1.52 g, 1.89 mmol) in 40 mL DCM, DCC (592 mg, 2.87 mmol) and NHS (325 mg, 2.82 mmol) were added and the resulting reaction mixture was stirred for 1 h at room temperature. The precipitated dicyclohexylurea was removed by filtration and washed twice with 5 mL DCM.

To the resulting clear yellow reaction mixture propargylamine (245 µL, 3.82 mmol) and TEA (525 µL, 3.79 mmol) were added. The reaction mixture was stirred for 1 h at room temperature and subsequently washed with 20 mL water. The organic phase was concentrated under reduced pressure and the resulting solid was purified by chromatography (21 g silica gel (40-63 µm DCM/MeOH—98:2→95:5). 1.01 g referring to a yield of 64% of the product CES0596 were obtained. According to RP-HPLC analysis the product contained no detectable impurities. The molecular weight and identity of (C) were confirmed by MALDI-MS and NMR Example 1.3

Synthesis of R-α-Lipoic-Acid-mPEG8 (D)

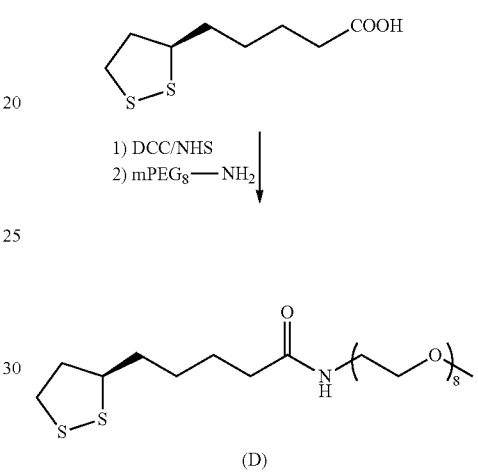

To a solution of R-α-lipoic-acid (538 mg, 2.61 mmol) in 40 mL DCM, DCC (8.11 mg, 3.93 mmol) and NHS (450 mg, 3.91 mmol) were added and the resulting reaction mixture was stirred for 1 h at room temperature. The precipitated dicyclohexylurea was removed by filtration and washed twice with 5 mL DCM. To the resulting clear yellow reaction mixture NH2-mPEG8 (0.98 g, 2.56 mmol) and TEA (725 µL, 5.23 mmol) were added. The reaction mixture was stirred for 1 h at room temperature and subsequently washed with 30 mL water. The organic phase was concentrated under reduced pressure and the resulting solid was purified by chromatography (34 g silica gel (40-63 µm) DCM/MeOH—98:2→97:3). 1.12 g referring to a yield of 75% of the product (D) were obtained. According to RP-HPLC analysis the product had a purity of approx. 99.8%. The molecular weight and identity of CES0598 were confirmed by MALDI-MS and NMR Example 1.4

Synthesis of R-α-Lipoic-Acid-5 kDa PEG-Allyl (F)

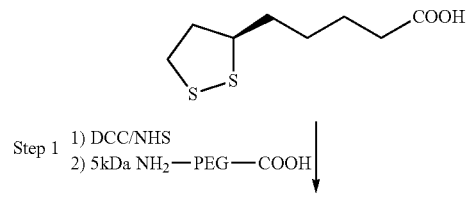

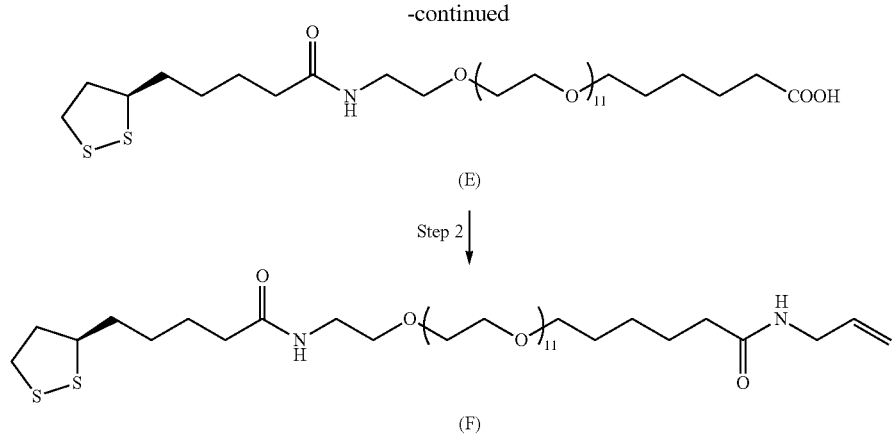

(E)

Step 2 ↓

(F)

Step 1: To a solution R-α-lipoic-acid (125 mg, 606 µmol) in 5 mL DCM, DCC (184 mg, 892 µmol) and NHS (108 mg, 938 µmol) were added and the resulting reaction mixture was stirred for 1 h at room temperature. The precipitated dicyclohexylurea was removed by filtration and washed twice with 2 mL DCM. To the resulting clear yellow reaction mixture NH2-5 kDa PEG-COOH (3.03 g, 606 µmol) and TEA (166 µL, 1198 µL) in DCM (91 mL) were added. The reaction mixture was stirred for 17 h at room temperature and subsequently washed with 50 mL 100 mM citric acid. The organic phase was concentrated under reduced pressure and the resulting solid matter was purified by chromatography (36 g silica gel (40-63 µm DCM/MeOH—98:2→90:10+0.1% AcOH). 2.75 g referring to a yield of 88% of the product (E) were obtained. According to RP-HPLC analysis, the product had a purity of approx. 80% with 20% of unknown impurities. These impurities were removed during the purification of the next step.

Step 2: To a solution of (E) (1.30 g, 251 µmol) in 40 mL DCM, DCC (76 mg, 368 µmol) and NHS (42 mg, 365 µmol) were added and the resulting reaction mixture was stirred for 6 h at room temperature. To the yellow slightly turbid solution allylamine (50 µL, 666 µmol) and TEA (100 µL, 721 µmol) were added and the mixture was stirred for 18 hrs. at room temperature. The precipitated dicyclohexylurea and free N-hydroxysuccinimide were removed by filtration and washed twice with 10 mL DCM. The reaction mixture was washed with 30 mL water. The organic phase was concentrated under reduced pressure and the resulting solid was purified by chromatography (31 g silica gel (40-63 µm DCM/MeOH—95:5→80:20). 1.18 g referring to a yield of 90% of the product (F) were obtained. According to RP-HPLC analysis the product had a purity of approx. 97.5%. The molecular weight and identity of (F) were confirmed by MALDI-MS and NMR.

Example 1.5

Synthesis of R-α-Lipoic-Acid-5 kDa PEG-Propargyl (G)

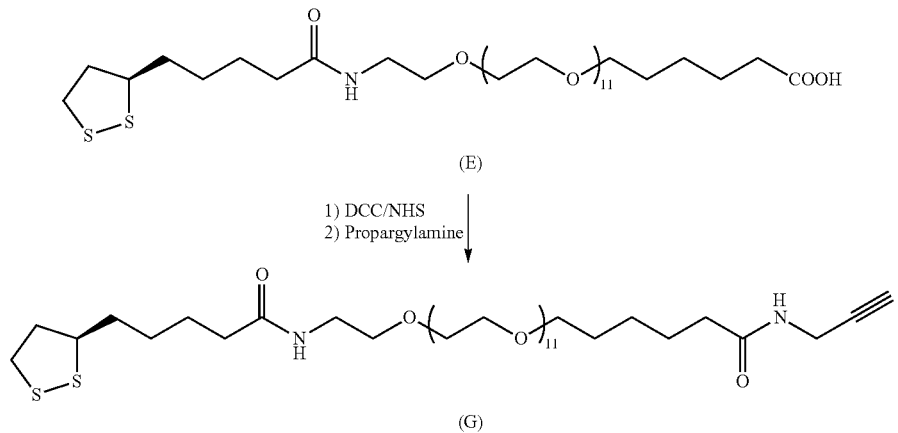

(E)

1) DCC/NHS
2) Propargylamine ↓

(G)

To a solution of product (E) obtained according to Step 1 of Example 1.4 (1.30 g, 251 µmol) in 40 mL DCM, DCC (116 mg, 562 µmol) and NHS (59 mg, 513 mmol) were added and the resulting reaction mixture was stirred for 3.5 hrs. at room temperature. To the yellow slightly turbid solution propargylamine (48 µL, 749 µmol) and TEA (104 µL, 750 µmol) were added and the mixture was stirred for 20 hrs. at room temperature. The precipitated dicyclohexylurea and free N-hydroxysuccinimide were removed by filtration and washed twice with 10 mL DCM. The reaction mixture was washed with 30 mL water. The organic phase was concentrated under reduced pressure and the resulting solid matter was purified by chromatography (32 g silica gel (40-63 µm DCM/MeOH—95:5→80:20). 1.18 g referring to a yield of 90% of the product (G) were obtained. According to RP-HPLC analysis the product had a purity of approx.

95%. The molecular weight and identity of (G) were confirmed by MALDI-MS and NMR.

Example 2

Example 2.1. Investigation of the Photochemical Coupling Conditions

A model system was used to establish the photochemical reaction of R-α-lipoic-acid-PEG12-allyl (B) with 3-mercapto propionic acid (Scheme 7):

bility of the photo initiated coupling of thiol reagents to the alkyne group of the synthesized cross-linker.

Further experiments were performed to determine velocity of the reaction and dependency on the reaction volume. During a period of 300 seconds approx. 60% of conversion was obtained and a linear regression described the reaction process well. Conversion did not depend on the applied reaction volume. Reaction volumes of 20 μL or 200 μL resulted in the same conversion in the same reaction time. In contrast, typical kinetics of such reaction types (*Macromol. Rapid Commun.* 2010, 31, 1247-1266) show a logarithmic

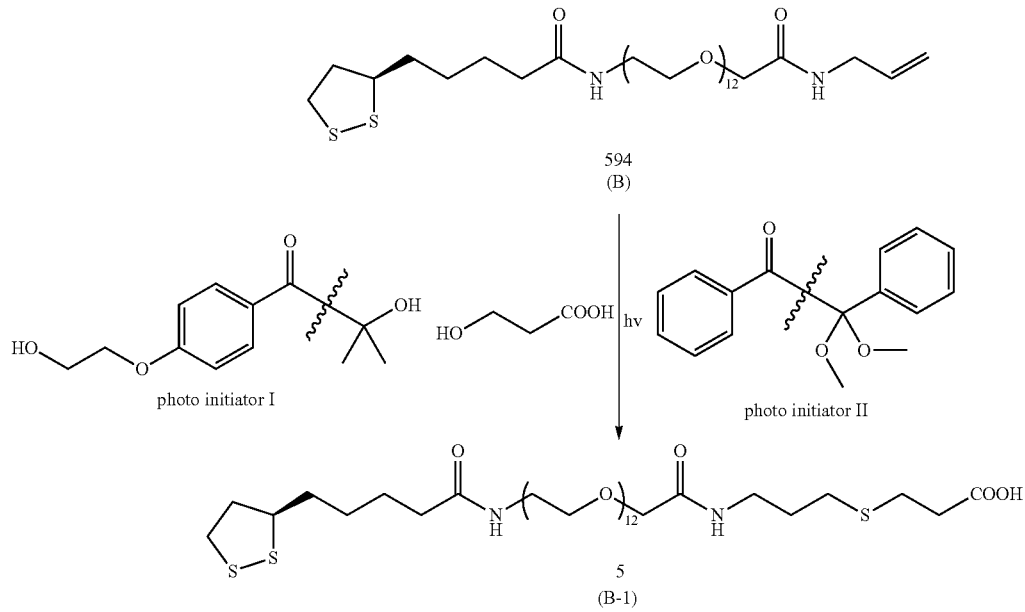

The optimized conditions were used to investigate the photochemical modification of a partially reduced antibody.

All experiments were performed using only photo initiator I (2-Hydroxy-4'-(2-hydroxyethoxy)-2-methylpropiophenone) since photo initiator II (2,2-Dimethoxy-2-phenyphenone) showed insufficient solubility in aqueous solutions (<1 mg/mL 10% DMSOaq). In contrast, photo initiator I was soluble in water up to a concentration of 1 mg/mL without addition of DMSO.

In initial experiments, a stock solution of product (B) of 1 mg/ml in water was treated with 10 mol % photo initiator I. The reaction mixture was separated into 5 tubes (200 μl per tube, A-E). To these tubes different molar excesses of 3-mercapto propionic acid (SH) were added (see Table 1, entry A to E).

| Tube | Eq. SH |
|------|--------|
| A    | 5      |
| B    | 25     |
| C    | 50     |
| D    | 100    |
| E    | 250    |

The reaction was induced using the following conditions:
Reaction temperature=1° C.
Light exposure time=30 min
$\lambda_{max}$: 310 nm
Immediately after irradiation samples were analyzed by HPLC. In summary, these experiments demonstrated feasicorrelation. This feasibility study focused on the reproducibility of this photo induced click reaction rather than full conversion. In this regard, a reproducible conversion of 2% was already obtained after 5 seconds.

Furthermore, based on these results the first experiments with a reduced antibody were designed. For reaction development only the 5 kDa PEG conjugates (alkene (F) and alkyne (G)) were used, as due to the mass difference the respective reaction products could be detected by SDS-PAGE.

Example 3

3.1. Partial Reduction of Antibodies

Free thiol groups can be introduced to antibodies by partial reduction of the antibody's internal disulfide bonds. Therefore reducing conditions should be investigated that result in partial reduction of the antibody without affecting its activity. Reactions should be performed in a volume of 25-50 μL. DTT, TCEP and cysteamine should be tested as reducing agent. Partially reduced antibody should then be modified with 5 kDa mPEG-Maleimide, which reacts with free sulfhydryl groups to investigate the success of the reduction reaction.

3.2. Experimental

Reducing agent screening—The reducing agent screening experiments were performed at protein concentrations of 0.5 mg/mL (anti-ACTH antibody) or 0.5, 5, 10 and 15 mg/mL (IgG1) using varying reducing agents excesses as indicated in the results section. The reactions were performed at room temperature for 1 or 2 h in final volume of 25 μL using 20 mM Na phosphate pH 7.2 as reaction buffer.

PEGylation of the antibodies—The PEGylation reaction was performed at room temperature for 3 h in 20 mM Na phosphate pH 7.2 at a molar PEG: protein ratio of 400:1. Protein concentrations in the reaction mixture ranged from 0.3 mg/mL (anti-ACTH antibody) to 0.3, 3, 6 and 9 mg/mL (IgG1).

SDS-PAGE—SDS-PAGE was performed under reducing or non-reducing conditions, using 4-12% Bis-Tris gels of the NuPAGE system from Invitrogen. Gels were stained with SIMPLYBLUE™ SafeStain kit (Invitrogen).

Size exclusion chromatography—SEC was performed on an Agilent 1200 using Superdex 200 10/300. SEC was performed at a flow rate of 0.65 mL/min. using PBS (10 mM $Na_2HPO_4$, 2 mM $KH_2PO_4$, 137 mM NaCl, 2.7 mM KCl, pH 7.4) as eluent.

3.2. Results

In initial experiments partial reduction of an anti-ACTH antibody was investigated using different concentrations of the reducing agents. In this way the concentration of the reducing agents should be determined at which complete, undissociated IgG can be obtained.

A generic murine IgG1 antibody (Biogenes) was used to investigate suitable conditions for partial reduction in more detail.

In particular, the impact of the IgG1 concentration on reduction efficacy was investigated for DTT. 5 kDa mPEG-Maleimide was added at high excess (400-fold) to reaction mixtures in order to detect all generated free thiol groups quantitatively as a band shift in SDS-PAGE.

Generally, with increasing excess of reducing agent higher ratios of reduced IgG1 were detected. Additionally, at higher protein concentrations lower DTT excesses were required to induce reduction of IgG1. Using a 6 or 10 eq. DTT, 0-5-fold modification of the heavy chain with 5 kDa mPEG-Maleimide was obtained according to SDS-PAGE analysis. Reduction with 1.5 or 3 eq. DTT resulted mainly in mono-PEGylation of the heavy chain, however, higher degrees of modification were also observed to a lesser extent. Only mono-modification of the light chain was observed at ratios of 1% (1.5 eq. DTT) to approx. 20% (10 eq. DTT).

Furthermore, the more IgG1 was in the reduced form, the higher the degree of PEGylation. The impact of disulfide reduction on the assembly state of IgG1 after addition of reducing agent and PEG was further analyzed by SEC Non-reduced IgG1 eluted at 20.1 min as a single and regular peak. Treatment with a 10-fold excess of DTT had no detectable effect on retention time or profile of the antibody indicating integrity under physiological conditions. This finding was in contrast to the findings by SDS-PAGE in which dissociation of IgG1 into heavy and light was observed under the same conditions.

Modification of the partially reduced IgG1 (10-fold excess of DTT) with 5 kDa mPEG-Mal resulted in broadening of the peak to lower retention times between 14.5 and 22 min. This was expected for a full antibody modified with 5 kDa mPEG. Signals at higher retention times that would have indicated dissociation of the antibody were not observed.

At lower DTT excess (1.5-fold), the peak obtained during SEC was less broad compared to 10-fold DTT excess, indicating a lower degree of PEGylation.

The impact of the reducing time was investigated for all three reducing agents at varying molar excesses using anti-ACTH antibody. After 1 h and 2 h of incubation reduction was stopped by addition of a high molar excess of 5 kDa mPEG-Maleimide.

Under all investigated conditions whole anti-ACTH antibody was observed by SDS-PAGE, indicating incomplete reduction of the interchain disulfide bonds. However, at increasing excesses of DTT or TCEP higher ratios of heavy and light chain as well as a higher degree of PEGylation were detected. The effect was slightly stronger at 2 h reducing time. Using cysteamine no notable dissociation of anti-ACTH antibody at 300-900-fold excess of reducing agent could be obtained. Based on these results it was decided to use 1 h reducing time. Furthermore, for preparation of PEGylated anti-ACTH antibody TCEP was chosen as reducing agent, as it is not modified with Maleimide activated molecules.

Example 4

Example 4.1. Coupling of PEG-Alkene/-Alkyne to Partially Reduced Antibodies by Photoreaction Photoreaction conditions for the coupling of antibodies to the alkene/alkyne function of the PEG-linker (F) and (G) have been developed. Therefore, different reaction conditions like light exposure time, PEG-excess, photo initiator I ("Photo I") concentration, protein concentration and reaction pH value shall be investigated. The coupling efficiency has been analyzed by SDS-PAGE of the resulting conjugates.

4.2 Experimental (Partial) reduction of antibodies—To an antibody solution with a protein concentration of 15 mg TCEP was added at a final concentration between 0.01 and 1 mM, corresponding to a molar excess of 0.1 and 10-fold over the antibody. The reducing reaction was performed in 20 mM Na phosphate pH 7.2 for 1 h at room temperature. Subsequently the antibody was modified with PEG-alkene or PEG-alkyne by photo click chemistry.

Modification of antibodies with PEG-alkene/-alkyne by photo click chemistry—Modification of the antibodies with PEG-alkene lot CES0601 or PEG-alkyne lot CES0602 was performed by photo induction using a CAPROBOX™ (Caprotech) under varying conditions as described in the following section.

4.3. Results

For initial photochemical coupling experiments of the PEG-alkenes the commercially available antibody IgG1 (mouse) was used. The antibody was reduced with 1 mM TCEP (10 eq.) at a protein concentration of 15 mg/mL for 1 h. The impact of PEG-excess on antibody modification was tested with reduced IgG1 using the following conditions:
  IgG1 concentration: 1 mg/mL
  Reaction buffer: 20 mM Na phosphate, pH 7.2
  Molar PEG-alkene (F) excesses over IgG1: 0.2- to 10-fold
  Photoinitiator I excess: 0.1 mol/mol PEG
  Light exposure time: 30 min.

PEGylation of IgG1 was monitored by SDS-PAGE analysis

By SDS-PAGE two bands at 55 kDa and 25 kDa were detected for the reduced but not PEGylated IgG1, which were assigned to the heavy and light chain respectively. For all samples conjugated with PEG-alkene by photo induction several high molecular weight bands were observed. These bands probably correspond to aggregated or incorrectly assembled protein as they did not match the expected molecular weight difference of approx. 10 kDa for a PEGylated antibody fragment. Only at a PEG-excess of 10 eq. a band at approx. 65 kDa was observed, which was assigned to the mono-PEGylated heavy chain. For an IgG1 sample that contained PEG and photo initiator but was not exposed to light, no additional bands aside from the heavy and light chain were detected. This indicates that aggregation was caused by light exposure.

As PEGylated heavy chain was obtained, it was assumed that modification of the antibody by photo click chemistry is feasible but the reaction had to be optimized towards reduction of aggregated antibody.

In order to reduce protein aggregation and increase PEGylation different light exposure times and photo initiator I concentrations were investigated. Therefore IgG1 reduced with TCEP was modified with PEG-alkene using the following conditions:

IgG1 concentration: 1 mg/mL
Reaction buffer: 20 mM Na phosphate, pH 7.2
Molar PEG-alkene excess over IgG1: 10-fold
Photo initiator I excess: 1-10 mol/mol PEG
Light exposure time: 5 s-10 min Increase of photo initiator I excess resulted in higher fractions of aggregates at all light exposure times, whereas the ratio of mono-PEGylated heavy chain was not affected. By reduction of light exposure to 5-30 seconds the fraction of aggregates could notably be reduced, however at this time range also the fraction of mono-PEGylated heavy chain decreased with the exposure time.

In order to minimize a possible incorrect assembly via interchain disulfide formation, it was decided to reduce the excess of TCEP over IgG1 to 1 or 5 eq. during the initial antibody reduction. Subsequently the antibody was modified with 1 eq. PEG-alkene using 1 eq. photo initiator I at different light exposure times By reduction of the TCEP excess, the ratio of aggregates could be decreased towards approx. 9% using 1 eq. TCEP at a light exposure time of 10 min. However, as a short light exposure is aspired for the final chip coating process, it was decided to choose a standard time of 0.5 min, which resulted in 13% mono-PEGylated heavy chain at 1-fold and 15% at 5-fold TCEP excess. Furthermore approx. 1% and 3% mono-PEGylated light chain were detected at 1 and 5 eq. TCEP, respectively. As at 1 eq. TCEP a notably lower fraction of aggregates was detected, it was decided to choose it as the standard TCEP excess.

The PEG-excess was further optimized for the standard light exposure time using the following conditions:

IgG1 concentration: 1 mg/mL
Reaction buffer: 20 mM Na phosphate, pH 7.2
Molar PEG-alkene excesses over IgG1: 0.5-10-fold
Photo initiator I excess: 1 mol/mol PEG
Light exposure time: 30 s With increasing PEG-excess a higher fraction of mono-PEGylated heavy chain was observed.

The highest ratio (7%) of mono-PEGylated heavy chain was obtained at 10 eq.

PEG, which was therefore chosen as the standard PEG-excess.

The protein concentration in the reaction mixture was optimized using the following reaction parameters:

IgG1 concentration: 0.2-10—mg/mL
Reaction buffer: 20 mM Na phosphate, pH 7.2
Molar PEG-alkene excess over IgG1: 10-fold
Photo initiator I excess: 1 mol/mol PEG
Light exposure time: 30 s The fraction of mono-PEGylated heavy chain increased at higher protein concentrations. However, the fraction of high molecular weight impurities (aggregates and multiply PEGylated antibody) increased as well.

The highest fraction of mono-PEGylated heavy chain (16%) was detected at a protein concentration of 2 mg/mL. However, in order to obtain a high protein concentration, the antibody has to be concentrated in a previous step. For the aspired coating of the chip the antibody, the concentrations of the antibodies and PEG: protein ratios will have to be further optimized. Therefore for the reaction in solution a standard protein concentration of 1 mg/mL was chosen, in order to minimize pre-concentration of the antibody.

The reaction pH value was optimized using the following reaction parameters:

IgG1 concentration: 1 mg/mL
Reaction buffers and pH values: 100 mM Na acetate, pH 5.0; 20 mM Na phosphate pH 7.2; 100 mM Na borate, pH 9.0
Molar PEG-alkene excess over IgG1: 10-fold
Photo initiator I excess: 1 mol/mol PEG
Light exposure time: 30 s At reaction pH 5, the highest fraction of mono-PEGylated light chain (2%) was detected, however a low ratio (6%) of mono-PEGylated heavy chain was obtained. Only a slightly higher ratio (7%) mono-PEGylated light chain was observed at pH 7. At pH 9, the highest fraction (9%) of mono-PEGylated was detected, but also the highest ratio of HMWI (22%) was obtained. It was therefore decided to use a standard reaction pH value of 7, at which less (18%) HMWI were detected.

The following standard reaction parameters were chosen:
Protein concentration: 1 mg/mL
Reaction buffer: 20 mM Na phosphate pH 7.2
Molar PEG-alkene/-alkyne excess over IgG1: 10-fold
Photo initiator I excess: 1 mol/mol PEG
Light exposure time: 30 s The standard reaction parameters were transferred to PEG-alkyne and modification of anti-ACTH antibody. As reduction of IgG1 and anti-ACTH antibody was obtained at different reducing agent in previous experiments, different TCEP concentrations were investigated.

For both conjugates (using PEG-alkene or PEG-alkyne) the highest fraction of mono-PEGylated protein (approx. 7%) was obtained at the lowest TCEP excess (0.1 eq.), which was therefore chosen as standard the condition.

According to non-reducing SDS-PAGE, PEGylation of anti-ACTH antibody at cysteine residues did not affect the quaternary structure of the antibody. In reducing SDS-PAGE of the conjugates bands at 66 and 75 kDa were detected, which were assigned to mono- and di-PEGylated heavy chain respectively. PEGylated light chain was not observed by SDS-PAGE.

Example 5

Introduction of thiol groups using N-succinimidyl S-acetylthioacetate (SATA) and subsequent modification with PEG-alkene According to SEC analysis the quaternary structure of the antibodies was not affected by partial reduction and conjugation of PEG to the respective cysteine residues. However reduction of disulfide bonds might weaken the antibody stability and interfere with its activity. Therefore, introduction of free thiol groups by use of the bi-functional reagent SATA should be investigated. By this approach SATA is initially attached via its NHS function to free amino groups of lysine residues in the antibody. Subsequently the sulfhydryl group of the conjugated SATA is de-protected by treatment with hydroxylamine:

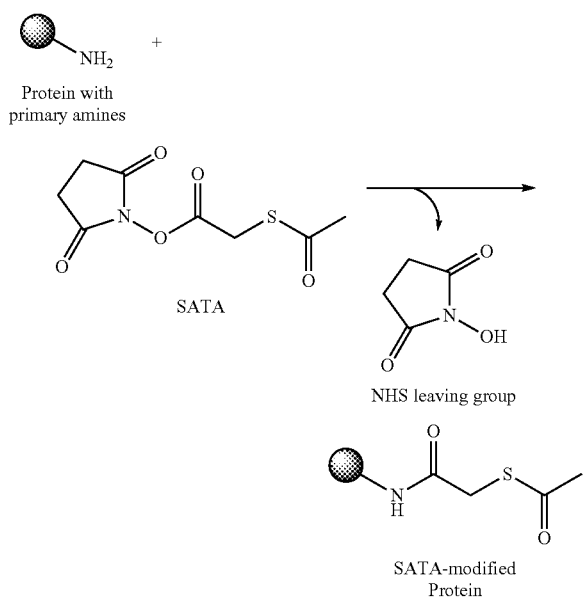

Deprotection of Sulfhydryl Group by Treatment with Hydroxylamine:

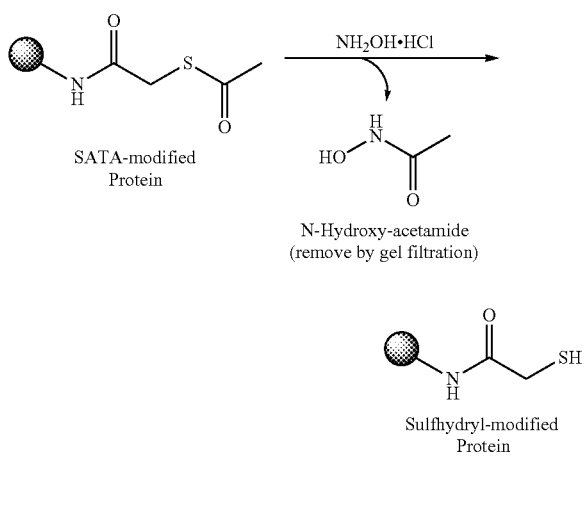

The resulting free thiol group should be conjugated with PEG-alkene/-alkyne by photo reaction under previously developed conditions.

5.1. Experimental

Attachment of SATA to free amino groups of antibodies—For attachment of SATA to IgG1 and anti-ACTH antibody the SATA and Sulfhydryl Addition Kit (Thermo Scientific) was used. The reaction was performed based on the manufacturer's instructions. Antibody at a concentration of 1 mg/mL in 20 mM Na phosphate pH 7.2 was modified with SATA at molar excesses of 1, 3, 5 and 10 equivalents. The reaction was performed for 2 hrs. at room temperature. The sulfhydryl group of the conjugated SATA was deprotected by treatment with hydroxylamine at a concentration of 5 mg/mL for 2 h at room temperature. Residual free SATA and hydroxylamine were removed using CentriSpin 10 columns.

Conjugation of PEG-alkene/-alkyne to free SATA thiol groups—PEG-alkene/-alkyne was attached to the free thiol group of SATA conjugated to the antibodies by photo induction using a CAPROBOX™ (Caprotech). The reaction was performed at a protein concentration of 1 mg/mL and a 10-fold PEG-alkene/-alkyne excess in 20 mM Na phosphate pH 7.2. 1 mole photoinitiator I per mole PEG was added and a light exposure time of 30 s was chosen.

5.2. Results

In initial experiments, attachment of PEG-alkene to free thiol groups of SATA molecules attached to amino groups of antibody IgG1 was investigated using different SATA excesses. The resulting PEGylation reaction mixtures were analyzed by SDS-PAGE In non-reducing SDS-PAGE a main band at 155 kDa corresponding to the whole IgG1 was detected. Additional bands at lower molecular weight (approx. 135 and 110 kDa) were assigned to partially dissociated IgG1. The ratio of these bands increased with higher SATA excesses, which might indicate that attachment of SATA affected the quaternary structure of the antibody. Therefore the excess of SATA over antibody should be minimized. In reducing SDS-PAGE a band at 66 kDa which amounted to 1-2% of the total protein corresponded to the mono-PEGylated heavy chain. Additional bands at higher molecular weight were assigned to high molecular weight impurities (HMWI), which might correspond to aggregates or multiply PEGylated protein. For further investigation, a control reaction was performed, for which IgG1 was modified with 3 or 10 eq. SATA. Subsequently the photo click reaction was performed under standard conditions without addition of PEG-alkene.

In reducing SDS-PAGE bands referring to HMWI as observed in the PEGylation reactions were detected. As no PEG was added to the mixtures during the photo click reaction, these bands were assigned to aggregated protein.

In subsequent experiments attachment of PEG-alkene to SATA conjugated with anti-ACTH antibody at 1- and 3-fold excess by photo click chemistry was investigated.

Using anti-ACTH antibody, a lower ratio of aggregates was observed after the photo click reaction compared to IgG1. A band corresponding to the mono-PEGylated heavy chain of anti-ACTH antibody was detected by reducing SDS-PAGE analysis. Thus PEGylation of the antibody is considered feasible, however, the ratio of mono-PEG-HC was low (<1%).

Example 6

Surface modification of gold surface with alkene/alkyne and covalent coupling of proteins (antibodies) via photoreaction.

6.1. Equipment

The equipment listed in the following table is exemplary. Equipment of comparable quality from other manufacturers may be used instead.

| Description, type | Manufacturer (Country) |
|---|---|
| UV-Lamp UV3 | Thermo-Fisher (D) |
| 0.2 mL cups | VWR (D) |
| 1.5 mL cups | VWR (D) |
| Thermomixer comfort | Eppendorf (D) |
| Vortex shaker | Neolab (D) |
| pH-meter Innolab 1 | WTW (D) |
| 1000 µL, pipette | Eppendorf (D) |
| 2-100 µL pipette | Eppendorf (D) |
| 0.5-10 µL pipette | Eppendorf (D) |
| 15 mL screw cap tubes, PE sterile | Sarstedt (D) |
| Spotting Device S11 | Scienion (D) |

6.2. Materials

The materials listed in the following table are exemplary. Materials of comparable quality from other manufacturers may be used instead.

| Name/Abbreviation, common name | Quality/ Specification | Provider/ Manufacturer |
|---|---|---|
| PEG-alkene/-alkyne | (F)/(G) | Examples 1.4./1.5. |
| Antibody | | Distinct supplier |
| Sodium dihydrogen phosphate monohydrate (NaH$_2$PO$_4$·H$_2$O), | Ph. Eur. | E. Merck (DE) |
| Disodium hydrogen phosphate (Na$_2$HPO$_4$) | Ph. Eur. | E. Merck (DE) |
| Water, Rectapur | Deionized water | ProLabo/VWR (DE) |
| TCEP, Tris(2-carboxyethyl)phosphine hydrochloride | Powder, ≥98% | Sigma-Aldrich (DE) |
| Photoinitiator, 2-hydroxy-4-(2-hydroxyethoxy)-2-metylpropiophenone | >98.0% (HPLC) | TCI Deutschland GmbH (DE) |
| DMAC, N,N-Dimethylacetamide | 99.9% (GC) | Sigma-Aldrich (DE) |

6.3. Preparation of Solutions and Buffers 10 mM sodium phosphate buffer pH 7.2
Weigh 710 mg of disodium hydrogen phosphate in a 250 mL beaker and fill up with 250 mL ddH$_2$O; weigh 780 mg of sodium dihydrogen phosphate into another 250 mL beaker and fill up with ddH$_2$O
Fill 250 mL disodium hydrogen phosphate in a 500 mL beaker and titer with dihydrogen phosphate until pH 7.2 is reached.
Filter the solution into a 500 mL glass bottle, using a 0.2 µm polyether sulfone membrane filter.
Store the solution at room temperature for up to six months.
25 mg/mL TCEP stock solution in ddH$_2$O
Weigh 25 mg TCEP into a 1.5 mL screw cap tube.
Add 1 mL of ddH$_2$O
Vortex the tube until the TCEP is completely dissolved. Store at 4° C.
1 mg/mL photoinitiator in 20 mM sodium phosphate buffer, pH 7.2
Weigh 10 mg photoinitiator into a 15 mL screw cap tube.
Add 10 mL of 10 mM sodium phosphate buffer, pH 7.2. Shake the solution 10 min at 40° C. to dissolve the photoinitiator.
Pass the solution through a 0.2 µm polyether sulfone syringe filter.
Prepare the solution on the day of use.
10 mM solution of PEG-alkene/-alkyne in DMAC and gold surface modification
PEG-alkene/-alkyne is stored at −20° C.; thaw at room temperature for approx. 30 min.
Weigh appropriate mass PEG-alkene/-alkyne into a 15 mL screw cap tube (5000 Da PEG-Alkene→dissolve 500 mg in 1 mL DMAC to obtain 100 mM stock solution).
Vortex the PEG solution until the PEG is completely dissolved.
100 mM stock solution can be aliquoted and stored at −20° C.
Prepare working solution on the day of use therefore:
Dilute stock solution with DMAC to 10 mM working solution concentration.
Invert and vortex the solution to homogenize.
Pipette 10 µL 10 mM PEG-alkene/alkyne solution to cleaned (wash protocol) gold CMOS surface and let react for 60 min 20° C. in a glass petri dish within a fume hood.
Wash gold CMOS surface with ddH$_2$O within a 250 mL beaker for 10 s.
Dry gold CMOS surface with pressurized air.
Store dry until use at 20° C.
TCEP reduction of disulfide bonds
Pipette 20 µL Antibody (0.2 mg/mL, MW=150 kDa) into a 0.5 mL Cup.
Dilute the TCEP stock solution 1:100 two times and 1:2 with sodium phosphate buffer, to give a final TCEP concentration of 3× molar excess related to antibody concentration
Add 20 µL TCEP to the antibody
Incubate the reduction mixture 60 min at room temperature and agitation at 30 rpm.
Spotting and coupling of antibodies
Pipette 15 µL Spotting-buffer into a Genetix Plate
Add 2.24 µL of photoinitiator stock solution
Add 12.76 µL reduced antibody solution two times higher concentrated than spotting concentration
Spotting (standard spotting procedure)
Place the UV-Lamp in the Spotting device and expose to UV-light (λ=302 nm) for at least 4 min—up to 10 min with a distance of 10 mm above gold surface.
Wash with ddH$_2$O and dry with pressurized air
Block surface with desired blocking agent (blocking protocol)
Wash with ddH$_2$O and dry with pressurized air
Use CMOS for intended assay The upper part of FIG. 4 shows schematically the metal surface (1), which is modified by the cross-linker molecules (4) being covalently linked to the metal surface via the dithiol group, having a polyethylene glycol (PEG) group as spacer and a terminal allyl group. Upon adding a biomolecule, which has at least one sulfhydryl group (2), a photoinitiator and irradiation with UV light, the biomolecule is immobilized (3) on the surface via the cross-linker as shown in the lower part of FIG. 4.

Examples 7 to 9

The results of the different immobilization experiments are shown in the fluorescence pictures of FIGS. 1 to 3, which have been made, in order to assess the surface modification of CMOS chips.

The CMOS chips comprise 128 electrodes, each of which can be addressed via spotting (cp. Example 6). The corresponding spotting layouts are also shown.

Example 7

Influence of UV light and photo initiator in comparison with a lipoamide-PEG(11)-maleimide modified surface.

In the following experiment, fluorescence pictures have been taken from a CMOS chip, which consist of 128 gold-electrodes as sensor surface. Different dilutions and spotting puffer solutions have been used for spotting a polyclonal rabbit anti-ACTH antibody. Subsequently, a complete assay for ACTH has been carried out, adding ACTH to the surface. A monoclonal mouse anti-ACTH antibody binds after the addition to bound ACTH and can be visualized with fluorescence marked rabbit anti-mouse antibody.

The intensity of the fluorescence is directly proportional to the amount of the bound polyclonal rabbit anti-ACTH antibody. In FIG. 1 the different conditions of the photo reaction in comparison to a lipoamide-PEG(11)-maleimide modified surface are shown.
- A: A lipoamide-PEG(11)-maleimide modified surface with 10 min UV irradiation at 304 nm wavelength. Only a weak occurrence of fluorescence can be observed. This means that the immobilization reaction of the antibody had taken place only to a low degree.
- B: An R-α-lipoic-acid-PEG12-propargyl modified surface according to the invention with 7.5 min irradiation time. It is apparent that an immobilization of the antibody must have taken place, due to the higher fluorescence intensities.

It is noteworthy that no photo initiator had been used in the samples KIA5-KIA7, whereas samples KIA1-KIA4 were generated with photo initiator. All antibodies were previously treated with TCEP, wherein different excesses of TCEP (30×, 3× molar excess with respect to the concentration of the antibody) have been employed.
- C: An R-α-lipoic-acid-PEG12-propargyl modified surface without UV irradiation. It is apparent that only little immobilization of the antibody at the surface takes place without UV irradiation.
- D: Spotting-Layout KIA represents different reaction conditions of the polyclonal rabbit anti-ACTH antibody.
SPO: represents the spotting control, where only the spotting buffer has been applied.

Example 8

Immobilization of a monoclonal mouse anti-ACTH antibody with and without photo initiator In this experiment, the applicability of the photoreaction for the immobilization of monoclonal mouse antibodies has been demonstrated. The antibodies had been dyed directly with a fluorescence marked anti-mouse antibody. The corresponding results are shown in FIG. 2.

FIG. 2 shows the immobilization of a monoclonal mouse antibody with the aid of the photoreaction according to the invention on R-α-lipoic-acid-PEG12-propargyl modified surface and 4 min irradiation time.

A: A comparison of the efficiency of the immobilization with and without use of a photo initiator is shown. It is apparent, that the use of a photoinitiator achieves an intense and uniform immobilization of the monoclonal antibody. However, without photo initiator, the efficiency of the immobilization is less pronounced and the formation of zones can be recognized. Nevertheless, it can be assumed, that the reaction can also be conducted without photo initiator at sufficient irradiation time.

B: The spotting layout KIA corresponds to a polyclonal rabbit anti-ACTH antibody, which cannot be dyed.

SPO: represents the spotting control, where only the spotting buffer has been applied.

MIA: represents the monoclonal mouse antibody, wherein MIA1 MIA2 have been generated with and without photo initiator. All antibodies have been treated with TCEP previously.

Example 9

Comparison of allyl and propargyl functionalities as well as defined and non-defined PEG chain lengths.

In this experiment, the reactivity of allyl and propargyl groups has been compared. In addition, the difference of the reactivity of defined and non-defined PEG chain lengths has been investigated. Non-defined PEG chain lengths are those having an average molecular mass of 5 kDa. The assays have been carried out as described in example 7 with ACTH as analyte. The utilized CMOS chips have been pre-treated with a layer of benzocyclobutene (BCB), whereupon the interspaces between the electrodes show enhanced fluorescence. The antibodies have been applied in a 1:2 dilution series starting at 100 µg/mL. The corresponding results are shown in FIG. 3. Irradiation time was 4 min.

FIG. 3 shows the immobilization of a polyclonal rabbit anti-ACTH antibody with the photoreaction according to the invention on auf different modified surfaces.

A: R-α-lipoic-acid-5 kDa PEG-propargyl (Example 1.5) modified surface.

B R-α-lipoic-acid-PEG12-propargyl (Example 1.2) modified surface.

C: R-α-lipoic-acid-5 kDa PEG-allyl (Example 1.4) modified surface.

D: R-α-lipoic-acid-PEG12-allyl (Example 1.1) modified surface.

E: The spotting-layout KIA corresponds with a polyclonal rabbit anti-ACTH antibody, wherein KIA shows the highest concentration (100 µg/mL as spotting solution), whereas KIA4 contains the lowest concentration (12.5 µg/mL as spotting solution). It is apparent, that D shows the highest intensity of fluorescence. All the other modified surfaces show slightly lower intensities, but a specific immobilization can be noted here, too.

The invention claimed is:
1. A method for the immobilization of a biomolecule containing at least one sulfhydryl group on a chip surface to obtain a functionalized and modified gold electrode, wherein at least one thiol group of a cross-linker compound of formula (I) is covalently linked to at least one of the metal atoms of the electrode, which method comprises the steps of:

a) optionally treating the biomolecule with an reducing agent in order to cleave existing —S—S— bridges in the biomolecule, or
optionally treating the biomolecule with an acylation agent carrying a protected sulfhydryl group and de-protecting the sulfhydryl group;
b) contacting a modified gold electrode with the biomolecule, wherein the modified gold electrode comprises a cross-linker compound comprising:
i) a terminal thiol or dithiol group covalently linked to the gold electrode,
ii) a spacer group, which at the other terminal end is carrying
iii) an isolated double or triple bond;
wherein the cross-linker compound is a compound of formula (I):

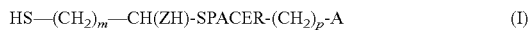

in which:
m is an integer from 2 to 6,
A is selected from —CH═CH$_2$ and

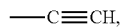

and
Z is S or a single bond, and
SPACER is a group of formula:

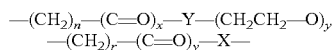

wherein:
X and Y are each independently NH or O,
n is 0 or an integer from 1 to 10,
x and y are each independently 0 or 1,
y is an integer from 1 to 20,
r and p are each independently selected from an integer from 1 to 6; and
c) irradiating the resulting surface with UV radiation in the presence of a photo-initiator to covalently link the biomolecule to the cross-linker and thereby obtain the modified and functionalized gold electrode.

2. A method according to claim 1, wherein Z is S, A is —CH═CH$_2$,
m is an integer from 2 to 4,
X and Y are NH,
n is 0 or an integer from 1 to 10,
x and v are 1,
y is an integer from 1 to 20, and
r and p are 1.

3. A method according to claim 1, wherein the biomolecule is an antibody, an enzyme or nucleic acid.

4. A method according to claim 1, wherein the photo-initiator is a 1-benzoyl-1-methyl-ethanol derivative.

5. A method according to claim 1, wherein the irradiation is carried out at a wavelength $A_{max}$ of 300 to 340 nm.

* * * * *